US009364388B2

(12) United States Patent
McCaney et al.

(10) Patent No.: US 9,364,388 B2
(45) Date of Patent: Jun. 14, 2016

(54) METHODS OF TREATMENT WITH NITRIC OXIDE AT PRESSURES GREATER THAN ONE ATMOSPHERE

(71) Applicant: Barry University, Miami Shores, FL (US)

(72) Inventors: Frank J. McCaney, New Haven, CT (US); Jeffrey L. Jensen, Palm City, FL (US); Christopher C. Miller, North Vancouver, CA (US); Daniel Packert, Pembroke Pines, FL (US); Gerhild Packert, Pembroke Pines, FL (US); Alex Stenzler, Long Beach, CA (US)

(73) Assignee: BARRY UNIVERSITY, Miami Shores, FL (US)

( * ) Notice: Subject to any disclaimer, the term of this patent is extended or adjusted under 35 U.S.C. 154(b) by 0 days.

(21) Appl. No.: 14/039,940

(22) Filed: Sep. 27, 2013

(65) Prior Publication Data

US 2014/0088490 A1    Mar. 27, 2014

Related U.S. Application Data

(60) Provisional application No. 61/706,189, filed on Sep. 27, 2012.

(51) Int. Cl.
*A61M 37/00* (2006.01)
*A61H 33/00* (2006.01)
(Continued)

(52) U.S. Cl.
CPC ............... *A61H 33/60* (2013.01); *A61F 13/00* (2013.01); *A61F 13/00063* (2013.01); *A61F 13/00068* (2013.01); *A61F 2013/0017* (2013.01); *A61F 2013/00165* (2013.01); *A61F 2013/00174* (2013.01); *A61F 2013/00182* (2013.01); *A61F 2013/00246* (2013.01); *A61F 2013/00285* (2013.01); *A61H 2033/0004* (2013.01); *A61H 2033/146* (2013.01); *A61M 35/00* (2013.01)

(58) Field of Classification Search
CPC ............... A61H 2033/0004; A61H 2033/146; A61H 33/60; A61H 33/14; A61H 2033/141; A61L 2300/114; A61L 2430/00; A61M 2202/0275
USPC ...................................................... 604/23, 24
See application file for complete search history.

(56) References Cited

U.S. PATENT DOCUMENTS

| 6,432,077 | B1 | 8/2002 | Stenzler |
| 6,793,644 | B2 | 9/2004 | Stenzler |

(Continued)

FOREIGN PATENT DOCUMENTS

| WO | 00/30659 | 6/2000 |
| WO | 2010/014818 | 2/2010 |

OTHER PUBLICATIONS

Bandarage et al., "Nitric Oxide-Releasing Nonsteroidal Anti-inflammatory Drugs: Novel Gastrointestinal-Sparing Drugs," *Mini Rev Med Chem*, 2001, 1:57-70.

(Continued)

*Primary Examiner* — Kevin C Sirmons
*Assistant Examiner* — Deanna K Hall
(74) *Attorney, Agent, or Firm* — Faegre Baker Daniels LLP

(57) ABSTRACT

The present invention provides methods of treatment by delivering nitric oxide at a pressure greater than 1 atmosphere (atm) to a subject in need thereof. Thus, the present invention provides an improved method of treating the skin surface of a subject, and below the skin surface of a subject.

29 Claims, 9 Drawing Sheets

(51) Int. Cl.
  *A61F 13/00* (2006.01)
  *A61M 35/00* (2006.01)
  *A61H 33/14* (2006.01)

(56) References Cited

U.S. PATENT DOCUMENTS

| | | | |
|---|---|---|---|
| 7,122,018 | B2 | 10/2006 | Stenzler |
| 7,520,866 | B2 | 4/2009 | Stenzler |
| 7,892,198 | B2 | 2/2011 | Stenzler |
| 2007/0088316 | A1 | 4/2007 | Stenzler et al. |
| 2008/0029093 | A1 | 2/2008 | Stenzler et al. |
| 2008/0193566 | A1 | 8/2008 | Miller et al. |
| 2011/0245759 | A1 | 10/2011 | McCaney |
| 2012/0283626 | A1* | 11/2012 | Belson et al. .......... 604/24 |

OTHER PUBLICATIONS

Bauer et al., "Evaluation of linear polyethyleneimine/nitric oxide adduct on wound repair : therapy versus toxicity," *Wound Repair Regen*, 1996, 6:569-77.

Chironna, "Chemical aspects of NOx scrubbing," *Pollution Engineering*, 1999, p. 33-36.

De Groote et al., "NO Inhibitions: Antimicrobial Properties of Nitric Oxide," *Clin Infect Dis*, 1995, 21(suppl 2):S162-164.

Delledonne et al., "The Functions of Nitric Oxide-Mediated Signaling and Changes in Gene Expression During the Hypersensitive Response," *Antioxid Redox Signal*, 2003, 5:33-41.

Fang, "Mechanisms of Nitric Oxiderelated Antimicrobial Activity," *Amer Soc Clin Invest*, 1997, 33:2818-25.

Frank "Large induction of the chemotactic cytokine RANTES during cutaneous wound repair : a regulatory role for nitric oxide in keratinocyte-derived RANTES expression," *Biochem J*, 2000, 347 Pt 1: 265-73.

Hardwick et al. "A novel method for the delivery of nitric oxide therapy to the skin of human subjects using a semi-permeable membrane," *Clinical Sci*, 2011, 100:395-400.

Hickey "Role of inducible nitric oxide synthase in the regulation of leucocyte recruitment," *Clin Sci*, 2001, 100:1-12.

Klevens, et al., "Invasive methicillin-resistant *Staphylococcus aureus* infection in the United States," 2007, *JAMA*, 298: 1762-1771.

Livermore, "Of Pseudomonas, porins, pumps and carbapenems," 2001, *J Antimicorb Chemother*, 47:247-50.

Miller "Nitric Oxide: The Future is Bright," *Journal for Respiratory Care Practitioners*, 2003, 10: 10-12.

Moncada et al., "Nitric Oxide: Physiology, Pathophysiology, and Pharmacology," *Pharmacol Rev*, 1991, 43:109-42.

Moran et al., "Methicillin-resistant *S. aureus* infections among patients in the emergency department," 2006, *N. Engl. J. Med.*, 355:666-674.

Omerod et al., The Inflammatory and Cytotoxic Effects of a Nitric Oxide Releasing Cream on Normal Skin, *J Invest Dermatol*, 1999, 113:392-7.

Pankey, 2005, "In vitro synergy of ciprofloxacin and gatifloxacin against ciprofloxacin-resistant Pseudomonas aeruginosa," *Antimicrob Agents Chemotherapy*;, 49:2959-2964.

Paramythiotou et al., "Acquisition of multidrug-resistant Pseudomonas aeruginosa in patients in intensive care units: role of antibiotics with antipseudomonal activity," 2004, *Clin Infect Dis*, 38:670-7.

Patel et al. "Biological aspects of reactive nitrogen species," *Biochim Biophys Acta*, 1999, 1411:385-400.

Shabini "Enhancement of wound repair with a topically applied nitric oxide-releasing polymer," *Wound Repair Regen*, 1996, 4:353-63.

Vasquez-Torres et al., "Therapeutic Applications of Nitric Oxide in Infection," *Nitric Oxide and Infection*, 1999, 475-88.

Weller et al., "A randomized trial of acidified nitrite cream in the treatment of tinea pedis," *J. Am Acad Dermatol*, 1998, 38:559-63.

Witte et al., "Role of nitric oxide in wound repair," *Amer J of Surg*, 2002, 183:406-12.

\* cited by examiner

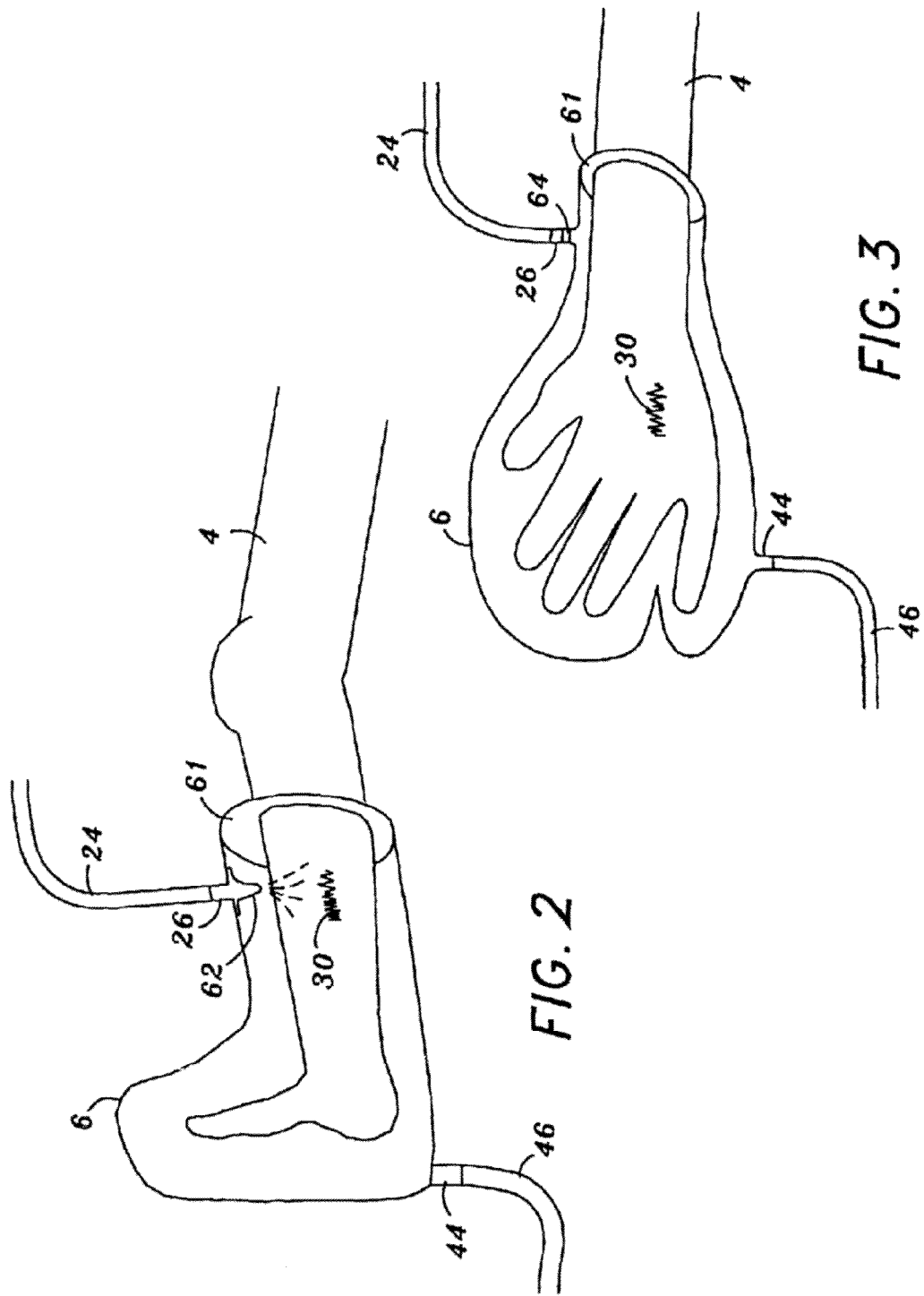

METHODS OF TREATMENT WITH NITRIC OXIDE AT PRESSURES GREATER THAN ONE ATMOSPHERE

CROSS-REFERENCE TO RELATED APPLICATIONS

The present application claims priority to U.S. Provisional Application No. 61/706,189, filed Sep. 27, 2012, which is hereby incorporated by reference in its entirety herein.

BACKGROUND OF THE INVENTION

In the 1980's, it was discovered by researchers that the endothelium tissue of the human body produced nitric oxide (NO), and that nitric oxide is an endogenous vasodilator, namely, an agent that widens the internal diameter of blood vessels. Prior to the 1980's, nitric oxide was most commonly known as an environmental pollutant that was produced as a byproduct of combustion. At high concentrations, inhaled nitric oxide is toxic to humans. At low concentrations, researchers have discovered that inhaled nitric oxide can be used to treat various pulmonary diseases in subjects. For example, nitric oxide has been investigated for the treatment of subjects with increased airway resistance as a result of emphysema, chronic bronchitis, asthma, adult respiratory distress syndrome (ARDS), and chronic obstructive pulmonary disease (COPD).

NO has been shown to play a critical role in various bodily functions, including the vasodilatation of smooth muscle, neurotransmission, regulation of wound healing and immune responses to infection such as bactericidal action directed toward various organisms (Moncada et al., 1991, Pharmacol Rev, 43: 109-42; De Groote et al., 1995, Clin Infect Dis, 21(suppl 2): S162-164). NO has been demonstrated to play an important role in wound healing through vasodilatation, angiogenesis, anti-inflammatory and antimicrobial action (Witte et al., 2002, Amer J of Surg, 183: 406-12). NO is a lipophilic signaling molecule with a small stokes radius that enables it to readily cross the plasma membrane into the cytosol. It is hypothesized that the antimicrobial and cellular messenger regulatory properties of this molecule, delivered in an exogenous gaseous form, might easily enter the wound milieu and be useful in optimizing the healing of chronic wounds with specific actions directed at reducing bacterial burden, reducing exudate and improving endogenous debridement.

The therapeutic potential of nitric oxide donors for cutaneous lesions, as a broad-spectrum antimicrobial seems promising (Fang, 1997, Amer Soc Clin Invest, 33: 2818-25; Vazquez-Torres et al., 1999, Nitric Oxide and Infection, 475-88). However, to date, this approach has not been realized in clinical application. This may be due to the toxic side effects of the carrier compounds of solid, liquid, cream, or other non-gaseous NO donors and the acidic environment required for release of the NO molecule (Omerod et al., 1999, J Invest Dermatol, 113: 392-7; Bauer et al., 1998, Wound Repair Regen, 6: 569-77). Endogenous approaches such as intracellular nitric oxide synthase (NOS) stimulation and wound dressings with either NO-donors or saturated NO-containing solutions have also failed to release consistent steady-state concentrations of NO (Shabini et al., 1996, Wound Repair Regen, 4: 353-63). Benjamin, and colleagues, describes a system using inorganic nitrite and an organic acid to produce NO on the skin surface (Weller et al., 1998, J Am Acad Dermatol, 38: 559-63). However, they describe the system as messy, impractical, causing pain in open wounds and possibly causing further damage to wounds. Recently, Hardwick, et al., refined the system using a selectively permeable membrane between the reactants and the wound. They reported that in an in vitro model it was effective at reducing microbial load (Hardwick et al., 2011, Clinical Sci, 100: 395-400).

It has been postulated that NO may be involved in wound macrophage infiltration regulation by down regulating cytokine-induced RANTES expression (Frank et al., 2000, Biochem J, 347 Pt 1: 265-73). NO may also reduce inflammation by its ability to scavenge reactive oxygen species (Bandarage et al., 2001, Mini Rev Med Chem, 1: 57-70; Patel et al., 1999, Biochim Biophys Acta, 1411: 385-400). While the inflammatory response is integral to wound healing, an aberrant inflammatory response is believed to be one causal factor in chronic wounds. NO inhibits platelet aggregation, assists in maintaining vascular tone, and inhibits mast cell degranulation (Hickey, 2001, Clin Sci, 100:1-12; Delledonne et al., 2003, Antioxid Redox Signal, 5: 33-41). NO produced constitutively by endothelial cells has been shown to have an on-going anti-inflammatory. This may in part be due to its effect on platelet aggregation. Inducible nitric oxide synthase (iNOS) is upregulated during the inflammatory response. Studies have shown that iNOS derived NO may also have anti-inflammatory characteristics effect (Hickey, 2001, Clin Sci, 100:1-12). Collectively, by maintaining vascular tone, promoting angiogenesis, moderating inflammation and inhibiting mast cell degranulation, NO can be viewed as an important molecule for exudate management. These actions of NO should nearly eliminate all but a "normal" level of exudate production.

Until recently, use of any oxide of nitrogen in the human model had not been contemplated. The discovery that NO is a significant messenger molecule in the cardiovascular system and capable of acting as a potent and specific pulmonary vasodilator resulted in the gaseous form of NO (gNO) being approved as an inhaled drug in the USA for the treatment of pulmonary hypertension of the newborn in 1999 (Miller, 2003, Journal for Respiratory Care Practitioners, 10: 10-12). There is now more than a decade of experience with the safe delivery, monitoring and understanding of NO in the clinical environment for vascular uses. With the experience of safe use and a better understanding of nitric oxide pharmacokinetics, interest has developed to closely examine the potential bacteriocidal effects of directly applied gaseous NO. Bactericidal effects of NO have been studied as far back as 1941 in the meat processing industry (Tarr, 1941, Nature, 147: 417-18). These original studies resulted in the use of nitrites in a mildly acidic environment forming nitrous acid, which dismutates to NO (Shank et al., 1962, Appl Bicrobiol, 10: 185-9).

Endogenous NO clearly plays a crucial role as an antimicrobial mediator in the human body. Although initially controversial, it is now well established that human macrophages generate NO as a primary mechanism of killing foreign microbes (MacMicking et al., 1997, Ann Rev Immunol, 15: 323-50). In both animal models and humans there is data that supports the concept that the inducible form of nitric oxide synthase (iNOS or NOS2) can be up-regulated by cytokines and bacterial products like lipopolysaccharide and lipoteichoic acid that are related to the body's response to infection (MacMicking et al., 1997, Ann Rev Immunol, 15: 323-50; Hibbs et al., 1992, J Clin Invest, 89: 867-77). Systemic nitrite and nitrate (end products of NO metabolism) levels are often elevated during infection (Ochoa et al., 1991, Ann Surg, 214: 621-6). It has also been reported that there is an upregulation of NOS or production of NO directly at the site of infection (Nicholson et al., 1996, J Exp Med, 183: 2293-2302; Stengler et al, 1996, J Exp med, 183: 1501-14).

Evidence that nitric oxide may play a role in the host defense mechanism is provided during exacerbation of infection through inhibition of nitric oxide synthases. NOS inhibitors are relatively selective, nontoxic compounds that inhibit this class of enzymes and can be administered to cultured cells, experimental animals, and people. The NOS inhibitors have been shown to worsen the course of diseases caused by an impressive array of phyla—viruses, bacteria, fungi, protozoa, and helminthes (Shank et al., 1962, Appl Microbiol, 10: 185-9). It has been reported that NOS expression is associated with good clinical outcomes in individuals infected with malaria (Anstay et al., 1999, Nitric Oxide and Infection). There are many studies that support enhancement of microbial proliferation by NOS inhibition in phagocytes and killing or inhibition of microbes by NO— donor compounds (De-Groote et al., Nitric Oxide and Infection).

Nitric oxide has also been investigated for its use as a sterilizing agent. It has been discovered that nitric oxide will interfere with or kill the growth of bacteria grown in vitro. PCT International Application No. PCT/CA99/01123, published Jun. 2, 2000, discloses a method and apparatus for the treatment of respiratory infections by nitric oxide inhalation. Nitric oxide has been found to have either an inhibitory and/or a cidal effect on pathogenic organisms.

While nitric oxide has shown promise with respect to certain medical applications, delivery methods and devices must cope with certain problems inherent with gaseous nitric oxide delivery. For example, exposure to very high concentrations of inhaled nitric oxide is toxic. Even lower levels of inhaled nitric oxide, however, can be harmful if the time of exposure is relatively high. For example, the Occupational Safety and Health Administration (OSHA) has set exposure limits for inhaled nitric oxide in the workplace at 25 ppm time-weighted averaged for eight (8) hours. It is extremely important that any device or system for delivering nitric oxide include features that diminish the leaking of significant amounts of nitric oxide into poorly ventilated spaces of the surrounding environment. If the device is used within a closed space, such as a hospital room or at home, dangerously high levels of nitric oxide can build up in a short period of time.

Another potential problem with using nitric oxide is that nitric oxide oxidizes in the presence of oxygen to form nitric dioxide, which when inhaled is toxic, even at levels lower than those of nitric oxide. If compensatory precautions are not taken, unacceptably high levels of nitric dioxide can develop, especially in closed, unventilated spaces. The rate of oxidation of nitric oxide to nitric dioxide is dependent on numerous factors, including the concentration of nitric oxide, the concentration of oxygen, and the time available for reaction. For example, in a mixture of 1000 ppm nitric oxide and 21% oxygen, it takes about 3.5 minutes for half of the nitric oxide to react to become nitric dioxide (Chironna and Altshuler, 1999, Pollution Engineering p. 33-36). Since nitric oxide will react with the oxygen in the air to convert to nitric dioxide, it is desirable to minimize incidental contact between the nitric oxide gas and the outside environment.

Another limitation of gaseous NO delivery to a subject is that the subject's skin provides a substantial barrier for effective delivery of NO to sites below the skin surface. This has restricted the use of gaseous NO to surface treatments. The skin barrier has thus prevented gaseous NO-based therapies at sites underneath the skin and within the body. Thus, there may be more clinical benefit for gaseous NO if it can be delivered below the outermost layer of the skin.

There remains a need for a device and method for the delivery of nitric oxide to treatment sites at the skin surface and below the skin surface. The present invention fulfills this need.

SUMMARY OF THE INVENTION

The present invention provides a method of delivering a gas mixture containing an effective amount of nitric oxide to a treatment site of a subject. The method comprises providing a flow-controlled source of a gas mixture containing nitric oxide; providing a bathing unit around the skin surface of the subject, with the bathing unit forming a seal with the skin surface of the subject, wherein the treatment site is at or beneath the skin surface of the subject; and transporting the gas mixture to the bathing unit so as to bathe the treatment site of the subject with the gas mixture at a pressure greater than 1 atmosphere.

In one embodiment the method comprises refreshing the treatment site with a fresh supply of the gas mixture.

In one embodiment, the method comprises monitoring the concentration of nitric oxide or nitric dioxide, bathing the treatment site.

In one embodiment, the method comprises evacuating the gas mixture from the treatment site. In one embodiment, the method comprises evacuating the gas mixture at a flow rate substantially equal to a flow rate of the gas mixture delivered to the skin surface. In one embodiment, the method comprises stripping at least one of nitric oxide and nitric dioxide from the evacuated gas mixture.

In one embodiment, the method comprises diluting the gas mixture.

In one embodiment, the method comprises adjusting the pressure of the gas mixture delivered to the treatment site.

In one embodiment, the method comprises controlling the flow rate of gas mixture into and out of the bathing unit.

In one embodiment, the treatment site is a wound. For example, in certain embodiments, the wound is a surgical wound, a trauma wound, or a burn.

In one embodiment, the treatment site is a lesion. For example, in certain embodiments, the lesion is a surgical wound, a trauma wound, a burn, an abscess, an actinic keratosis, a keloid, a scar, or skin cancer.

In one embodiment, the treatment site is an infection site. For example, in certain embodiments, the infection site is infected by at least one pathogen, including for example, a bacterium, a virus, a fungus, a parasite, an arthropod, a protozoan, and an antibiotic resistant bacterium.

In one embodiment, the subject has an inflammatory disorder, and the treatment site is affected by the inflammatory disorder. For example, in certain embodiments, the inflammatory disorder is psoriasis, dermatitis, eczema, or rosacea.

In one embodiment, the subject is in need of enhanced blood flow at the treatment site.

In one embodiment, the subject is in need of enhanced collagen synthesis at the treatment site.

In one embodiment, the subject is in need of angiogenesis at the treatment site.

In one embodiment, the subject is in need of hair growth at the treatment site.

In one embodiment, the subject has erectile dysfunction. For example, in one embodiment, the subject has erectile dysfunction and is in need of enhanced blood flow at the treatment site.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2 depicts a bathing unit surrounding the foot of a subject.

FIG. 3 depicts a bathing unit surrounding the hand of a subject.

DETAILED DESCRIPTION

Figure 1:
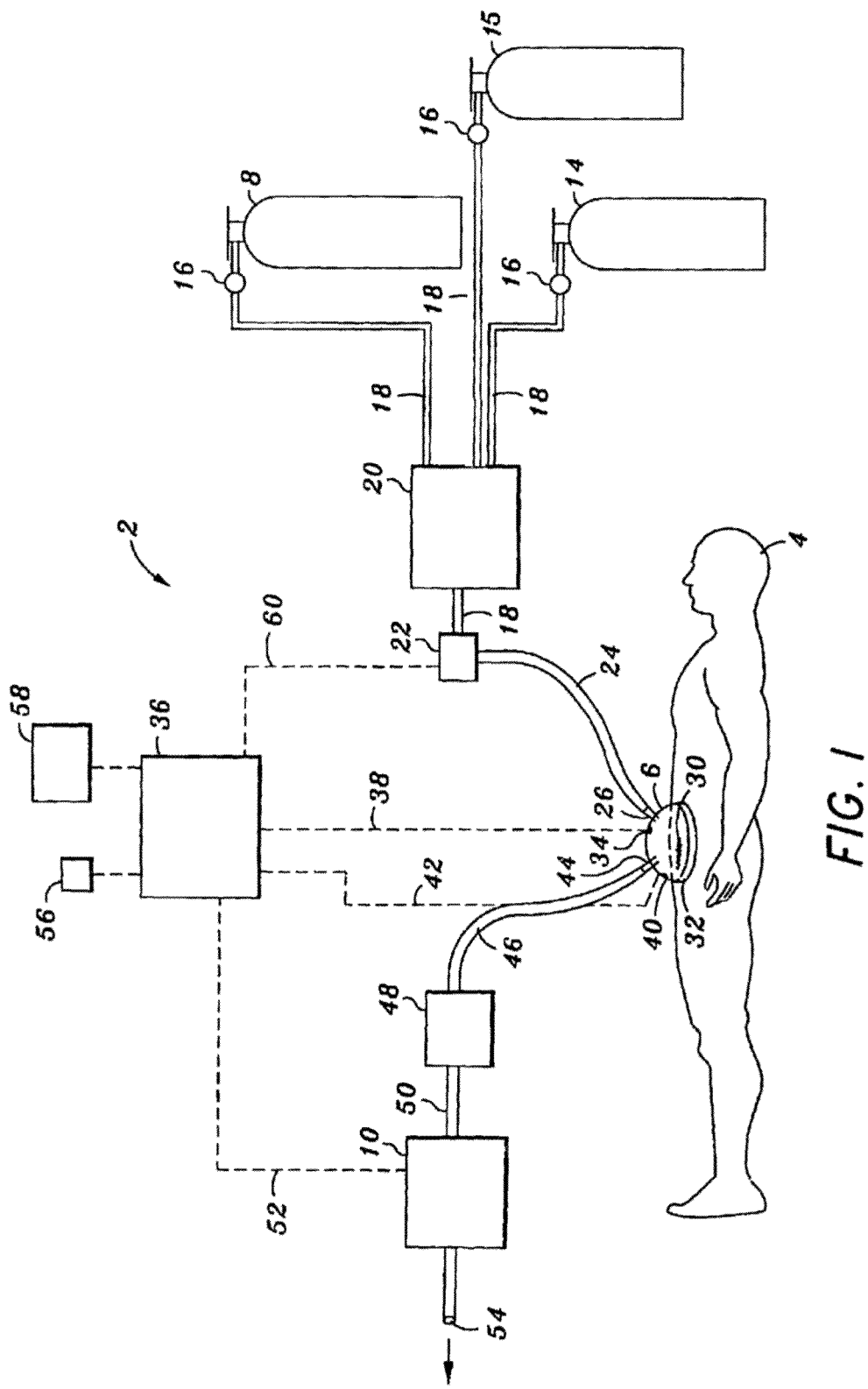
FIG. 1 depicts a schematic representation of an exemplary nitric oxide delivery device according to one aspect of the invention.

The present invention provides a method of treatment by delivering nitric oxide at a pressure greater than 1 atmosphere (atm) to a subject in need thereof. In certain embodiments, the present invention provides an improved method of delivering therapeutic nitric oxide to a treatment site located at the skin surface or below the skin surface.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the term "modulate" is meant to refer to any change in biological state, i.e. increasing, decreasing, and the like.

As used herein, a "therapeutically effective amount" is an amount of a therapeutic composition sufficient to provide a beneficial effect to a subject to which the composition is administered.

The terms "patient," "subject" and "individual" are interchangeably used to mean a warm-blooded animal, such as a mammal, suffering from a disease or disorder. It is understood that humans and animals are included within the scope of the term "subject," "subject" or "individual."

As used herein, the terms "treatment site" and "site of treatment" are used to mean an area, a region or a site on, or inside the body of, a subject, including a tissue, a wound, a lesion, an abscess, including intact skin. The treatment sites that can be treated by the methods of the invention include any area, region or site on the surface of, or inside the body of, a subject that can be exposed to gaseous nitric oxide. By way of nonlimiting examples, regions and sites that can be treated by the methods of the invention include, but are not limited to, external tissues (e.g. skin, etc.), internal tissues (e.g. mucosa, muscle, fascia, etc.), and internal organs (e.g. lungs, liver, etc.). It should be understood that many areas, regions and sites that are normally not amenable to exposure to gaseous nitric oxide can become amenable to exposure to gaseous nitric oxide after a wound, such as, for example, a surgical incision or traumatic laceration, is introduced to the body of a subject. Moreover, "treatment site" should not be construed to include only those areas, regions or sites that exhibit overt evidence of pathology, but rather should also be construed to include areas, regions or sites that may be asymptomatic, i.e., that do not contain overt evidence of pathology, but that may be affected nonetheless and that could, in time, exhibit more overt evidence of pathology. By way of nonlimiting examples, such a site can include a trauma wound, surgical wound, intact tissue or burn, including those that have come into contact with, or which is at risk of potentially coming into contact with, a pathogen that can colonize or infect the wound, and can be treated, or prophylactically treated, with the devices and methods of the invention.

The term "treat" or "treatment," as used herein, refers to the alleviation (i.e., "diminution") and/or the elimination of a sign or symptom or a source of a sign or symptom of a disease or disorder. By way of several non-limiting examples, a symptom of a bacterial infection can be treated by alleviating a symptom of that disorder. A symptom of a bacterial infection can also be treated by altogether eliminating a symptom of that disorder. A bacterial infection or colonization can be treated by alleviating the source, or "cause," of that disorder. A bacterial infection or colonization can also be treated by eliminating the source of that disorder.

"Evacuating" as the term is used herein, refers to the partial or complete removal of a substance from a specific region or area. This removal can be accomplished actively (e.g., vacuum or displacement) or passively (e.g., diffusion). By way of two separate non-limiting examples according to the present invention, nitric oxide gas can be partially removed from the area under an enclosed device which surrounds the site of treatment of a subject, or nitric oxide gas can be completely removed from the area under an enclosed device which surrounds a portion of the a site of treatment of a subject. In these examples, the nitric oxide gas may or may not be replaced with a "substitute" gas. The "substitute" gas, according to the invention, may be any gas, including nitric oxide gas.

As used here, the term "pathogen" refers to an infectious and/or parasitic organism, including, but not limited to, viruses, fungi, protozoa, parasites, arthropods, helminthes, and bacteria, including antibiotic-resistant bacteria.

Examples of fungi include, but are not limited to, *Epidermophyton floccosum, Epidermophyton* sp., *Microsporum canis, Microsporum gypseum, Microsporum* sp., *Trichophyton mentagrophytes, Trichophyton rubrum, Trichophyton tonsurans, Trichophyton verrucosum, Trichophyton* sp., *Exserohilum* sp., *Exophiala* sp., *Candida albicans, Candida glabrata, Candida guilliermondii, Candida krusei, Candida lusitaniae, Candida parapsilosis, Candida tropicalis, Candida* sp., *Cryptococcus gattii, Cyptococcus neoformans, Cyptococcus* sp., *Geotrichum* sp., *Malassezia* sp., *Pneumocystis jiroveci, Rhodotorula* sp., *Saccharomyces* sp., *Trichosporon* sp., *Blastomyces dermalitidis, Coccidioides immitis, Coccidioides posadasii, Coccidioides* sp., *Histoplasma capsulatum, Paracoccidioides brasiliensis, Penicillium marneffei, Sporothrix schenckii, Acremonium* sp., *Aspergillus flavus, Aspergillus fumigates, Aspergillus niger, Aspergillus* sp., *Alternaria* sp., *Aureobasidium* sp., *Bipolaris* sp., *Cladophialophora* sp., *Cladosporium* sp., *Fonsecaea* sp., *Hortaea werneckii, Madurella* sp., *Phialophora* sp., *Piedraia horlae, Wangiella dermatitidis, Absidia* sp., *Cunninghamella, Mucor* sp., *Rhizomucor* sp., *Rhizopus* sp. Examples of protozoa include, but are not limited to, *Acanthamoeba castellanii, Acanthamoeba* species, *Balamuthia mandrillaris, Endolimax nana, Entamoeba dispar, Entamoeba histolytica, Entamoeba moshkovskii, Entamoeba* species, *Hartmanella species, Lodamoeba butschlii, Naegleria fowleri, Naegleria species, Balantidium coli, Chilomastix memili, Dientamoeba fragi ils, Enteromonas hominis, Giardia Limblia, Leishsmania braziliensis* complex, *Leishmania donovani* complex, *Leishmania major, Leishmania mexicana* complex, *Leishmania tropica, Leishmania* species, *Retortamonas* in *Cestinalis, Trichomonas vaginalis, Trichomonas* species, *Trypanosoma brucei gambiense, Trypanosoma brucei rhodesiense, Typanosoma cruzi, Babesia* species, *Cryptosporidium hominis, Cryptosporidium parvum, Cyclospora cayetanensis, Isospora belli, Plasmodium falciparum, Plasmodium malariae, Plasmodium ovale, Plasmodium vivax, Sarcocystis hominis, Sarcocystis* species, *Toxoplasma gondii, Bracheola* species, *Encephalitozoon hellum, Encephalitozoon intestinalis, Encephalitozoon* species, *Enterocytozoon bieneusi, Nosema* species, *Pleistophora* species, *Thachipleistophora homin* is, *Vittaforma corneae,* and *Blastocystis hominis.*

As used herein, an "antibiotic-resistant bacterium," is a bacterium that is a member of a species of bacteria that has historically exhibited greater susceptibility to one or more particular antibiotic agents than the antibiotic-resistant member bacterium presently exhibits.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

It has been unexpectedly discovered in the present invention, that delivering a mixture of nitric oxide at a pressure greater than 1 atmosphere (atm) to a subject provides enhanced properties over the delivery of nitric oxide at normal atmospheric pressure. Thus, the present invention provides an improved method of treating sites at the skin surface, and below the skin surface, by applying gaseous nitric oxide at a pressure greater than 1 atm to the treatment site of a subject.

Nitric oxide is involved in a plethora of critical physiological processes and the lack of a mechanism for delivering active agent in sufficient doses to the site of action has prevented the potential for nitric oxide to impact favorably a large number of diseases. The delivery of nitric oxide at a pressure greater than 1 atm represents an improvement over existing devices and methods to deliver active nitric oxide at treatment sites throughout the body. As detailed herein, the delivery of nitric oxide, at a pressure greater than 1 atm, is able to penetrate the outermost layer of the skin, thereby exhibiting its clinical benefit at sites within the body and below the skin surface. Although in various embodiments of the invention described herein, the delivery of nitric oxide, at a pressure greater than 1 atm, exhibits enhanced properties over the delivery of nitric oxide at pressures less than 1 atm, the skilled artisan will understand that the invention described herein also includes nitric oxide delivered at any pressure, including pressures at 1 atm and at less than 1 atm.

The present invention provides an improved method of treating a subject by applying gaseous nitric oxide at a pressure greater than 1 atm to subject. For example, in one embodiment the present invention provides an improved method of treating an infection in a subject. In another embodiment, the present invention provides an improved method of treating an inflammatory disorder in a subject. In yet another embodiment, the present invention provides an improved method of treating erectile dysfunction in a subject. The invention also provides improved methods for enhancing blood flow, collagen synthesis, angiogenesis and hair growth. Further, the invention also provides improved methods for the treatment of scars and lesions.

In one embodiment, the present invention specifically provides a method of treating various infections in a subject in need thereof, including infections caused by a virus, a fungus, a protozoan, a parasite, a arthropod or a bacterium, including a bacterium that has developed resistance to one or more antibiotics. Examples of bacteria known to have developed resistance to one or more antibiotics include, but are not limited to, *Staphylococcus aureus, Pseudomonas aeruginosa, Streptococcus pneumoniae, Escherichia coli, Salmonella, Klebsiella,* and *Enterococci.* Examples of viral infections include human papilloma virus, herpes simplex I, herpes simplex II, hepatitis B, hepatitis C, influenza, measles, mumps, and rabies. Typically, gaseous nitric oxide, at a pressure greater than 1 atm, is administered to the site of infection of a subject using a device for delivery of the gas to the site of infection. Although not wishing to be bound by any particular theory, improved healing by the application of nitric oxide can occur by the reduction of the level of the pathogen, by the improvement of blood supply to the affected tissues through vasodilation, by the reduction of inflammation, or by a combination thereof.

In various embodiments, the methods of the invention are used to treat an infection in a subject in need thereof. In one aspect, the invention provides a method of treating a bacterial infection, such as, for example, an antibiotic-resistant bacterial infection, by applying gaseous nitric oxide, at a pressure greater than 1 atm, to a site of infection of a subject. In another aspect, the invention provides a method of treating a fungal infection by applying gaseous nitric oxide, at a pressure greater than 1 atm, to a site of infection of a subject. In still another aspect, the invention provides a method of treating a viral infection by applying gaseous nitric oxide, at a pressure greater than 1 atm, to a site of infection of a subject. In a further aspect, the invention provides a method of treating a parasitic infection by applying gaseous nitric oxide, at a pressure greater than 1 atm, to a site of infection of a subject. In a still further aspect, the invention provides a method of treating a protozoan infection by applying gaseous nitric oxide, at a pressure greater than 1 atm, to a site of infection of a subject.

In one embodiment, the present invention provides a method of treating inflammation. Typically, gaseous nitric oxide, at a pressure greater than 1 atm, is administered to the site of inflammation of a subject using a delivery device for the delivery of the gas to the site of inflammation. Non-limiting examples of inflammatory associated disorders where delivering nitric oxide at a pressure greater than 1 atm can be used for treatment include psoriasis, dermatitis (atopic, contact, sebborheic, etc), eczema, and rosacea. In one aspect, the invention provides a method of treating inflammation associated with an auto-immune disorder, such as for example psoriasis. Although not wishing to be bound by any particular theory, reducing inflammation by the application of nitric oxide at a pressure greater than 1 atm can occur by the down regulation of cytokine-induced RANTES expression, scavenging of reactive oxygen species, inhibition of platelet aggregation, maintenance of vascular tone, inhibition of mast cell degranulation, or by a combination thereof.

In another embodiment, the present invention provides a method of enhancing blood flow. Typically, gaseous nitric oxide, at a pressure greater than 1 atm, is administered to a site in need of increased blood flow of a subject using a delivery device for the delivery of the gas to the site. Non-limiting examples of conditions in which enhancement of blood flow via the application of nitric oxide at a pressure greater than 1 atm would be beneficial include ischemia-reperfusion injury. Although not wishing to be bound by any particular theory, enhancement of blood flow by application of nitric oxide can occur by the vasodilation of capillaries and blood vessels.

In another embodiment, the present invention provides a method for treating erectile dysfunction. Typically, gaseous nitric oxide, at a pressure greater than 1 atm, is administered to a treatment site using a delivery device for the delivery of the gas to the site. In one embodiment the treatment site is the penis of a subject.

In a further embodiment, the present invention provides a method of enhancing collagen synthesis. Typically, gaseous nitric oxide, at a pressure greater than 1 atm, is administered to a site in need of collagen synthesis of a subject using a delivery device for the delivery of the gas to the site. Non-limiting examples where the enhancement or induction of collagen synthesis by the application of nitric oxide at a pressure greater than 1 atm would be beneficial include wound healing and wrinkle removal. Non-limiting examples of the types of collagen, the synthesis of which can be enhanced by nitric oxide, include type I collagen, type II collagen, type III collagen, type IV collagen, type V collagen, type VI collagen, type VII collagen, type VIII collagen, type IX collagen, type X collagen, type XI collagen, type XII collagen, type XIII collagen, type XIV collagen, type XV collagen, etc.

In another embodiment, the present invention provides a method of enhancing or inducing angiogenesis. Typically, gaseous nitric oxide, at a pressure greater than 1 atm, is administered to a site of a subject in need of angiogenesis using a delivery device for the delivery of the gas to the site. Non-limiting examples of situations in which enhanced or induced angiogenesis, by the delivery of nitric oxide at a pressure greater than 1 atm, would be beneficial include cases of trauma, transplant, and in bypassing a vessel blockade that occurs, for example, in the heart or in peripheral artery disease.

In yet another embodiment, the present invention provides a method of minimizing lesions. Typically, gaseous nitric oxide, at a pressure greater than 1 atm, is administered to a lesion of a subject using a delivery device for the delivery of the gas to the site. Non-limiting examples of lesions which can be treated by the delivery of nitric oxide at a pressure greater than 1 atm include actinic keratosis, keloids, scars, and skin cancer.

In one embodiment, the present invention also provides a method of promoting hair growth. Typically, gaseous nitric oxide, at a pressure greater than 1 atm, is administered to a site in need of hair growth of a subject using a delivery device for the delivery of the gas to the site.

In an aspect of the invention, a device is applied to a treatment site to deliver nitric oxide at a pressure greater than 1 atm. The device preferably minimizes leaking to avoid the potentially dangerous build-up of nitric oxide and nitric dioxide concentrations in the surrounding environment. The application of nitric oxide to the affected region preferably decreases the time required to heal the affected area. Especially for deliveries of higher concentrations of nitric oxide, for example greater than 1000 ppm, the device optionally includes a nitric oxide and/or nitric dioxide absorber or scrubber that will remove or chemically alter nitric oxide and/or nitric dioxide prior to or during discharge from the delivery device.

In an aspect of the invention, the application of nitric oxide, at a pressure greater than 1 atm, such as for example, 1.1, 1.2, 1.3, 1.4, 1.5, 1.6, 1.7, 1.8, 1.9, 2.0, 2.5, 3.0, 3.5 or 4.0 or more atmospheres, enables the penetration of gaseous nitric oxide to affected tissues deeper than the surface of the body tissue. The delivery of gaseous nitric oxide to a treatment site at higher than atmospheric pressure serves to increase the penetration of the nitric oxide deeper into the treatment site and/or surrounding tissues. Thus, the invention provides a method of delivering nitric oxide to treatment sites not otherwise accessible.

In an aspect of the invention, the application of nitric oxide, at a pressure greater than 1 atm to the affected region decreases the time required to heal the affected area, induces healing of the affected area, or directly contributes to the healing of the area. In an embodiment of the invention, application of nitric oxide, at a pressure greater than 1 atm, to the affected region acts by two or more different mechanisms to promote healing.

In an aspect of the invention, the improvement of symptoms in a subject being treated with a device of the invention, a method of the invention, or both, and/or the promotion of healing, can be measured by any one of many ways known in the art. Generally, promotion of healing can be ascertained by the artisan skilled in treating the type of disorder being treated.

While the methods of the invention should not be construed to be limited solely to the mechanisms and devices described herein for delivery of nitric oxide, at a pressure greater than 1 atm, to a site requiring treatment, certain embodiments encompassing various mechanisms and devices are described herein as examples of how to perform the methods of the invention. It is understood that the methods of the invention may be practiced using other known or heretofore unknown mechanisms and devices and the invention should be construed to encompass all such mechanisms and devices as appropriate.

As would be understood by those skilled in the art, the present invention encompasses any known means or mechanisms for creating a source of pressurized gaseous NO. For example, gaseous NO, at a pressure greater than 1 atm, can be derived from a variety of sources including but not limited to, vacuum pumps, suction pumps, pneumatic pumps, chemical reactions, as well as sources created through electrical, magnetic, or mechanical means.

In a first aspect of the invention, a device for the delivery of nitric oxide gas, at a pressure greater than 1 atm, to a treatment site includes a source of nitric oxide gas, a bathing unit, and a flow control valve. Optionally, the device for the delivery of nitric oxide gas may also contain an absorber, and/or a scrubber, and/or a vacuum unit. The bathing unit is in fluid communication with the source of nitric oxide gas and is adapted for surrounding the treatment site. The flow control valve is positioned downstream of the source of gas and upstream of the bathing unit for controlling the amount of nitric oxide gas mixture that is delivered to the bathing unit. The optional vacuum unit may be positioned downstream of the bathing unit for withdrawing gas from the bathing unit.

In a second aspect of the invention, the device according to the first aspect of the invention includes a controller for controlling the operation of the flow control valve and an optional vacuum unit.

In a third aspect of the invention, the device according to the first aspect of the invention further includes a gas blender. The nitric oxide gas and the optional oxygen gas are mixed by the gas blender. The device also optionally includes a nitric oxide gas absorber or scrubber unit that is positioned upstream of the vacuum unit. The device further includes a controller for controlling the operation of the flow control valve and the vacuum unit.

In a fourth aspect of the invention, the device according to the first aspect of the invention further includes a source of a third dilutent gas. The third dilutent gas and the nitric oxide gas and the optional oxygen gas can be mixed together using a gas blender.

In a fifth aspect of the invention, a method of delivering an effective amount of nitric oxide to a treatment site includes the steps of providing a bathing unit around the treatment site. Gas containing the nitric oxide mixture is then transported to the bathing unit so as to bathe the site of infection with gaseous nitric oxide, at a pressure greater than 1 atm. Optionally, at least a portion of the delivered gas is evacuated or diffuses from the bathing unit.

A delivery device for the delivery of a nitric oxide gas mixture at a pressure greater than 1 atm to a site of infection is thus provided. The device is preferably constructed to limit the amount of nitric oxide-containing gas leaking from the delivery device. The method of delivering an effective amount of nitric oxide gas mixture at a pressure greater than 1 atm to a treatment site of a subject promotes healing or otherwise provides clinical benefit to the subject.

In one set of embodiments and referring now to FIG. 1 herein, a nitric oxide delivery device 2 is shown connected to a subject 4. In its most general sense, the nitric oxide delivery device 2 includes a bathing unit 6 that is fluidically connected to a nitric oxide gas source 8, a flow control valve 22, and an optional vacuum unit 10. FIG. 1 therefore illustrates one preferred embodiment of the device useful for administration of a nitric oxide gas mixture to a subject in the methods of the invention. Although FIG. 1 depicts a bathing unit 6 in contact with the surface of the mid-region of a subject, it should be understood that the bathing unit 6 can be modified as appropriate to bathe any site on the surface of, or inside the body of, a subject.

In FIG. 1, the nitric oxide gas source 8 is a pressurized cylinder containing nitric oxide gas. While the use of a pressurized cylinder is the preferable method of storing the nitric oxide-containing gas source 8, other storage and delivery means, such as a dedicated feed line (wall supply) or a nitric oxide generator can also be used. Typically, the nitric oxide gas source 8 is a mixture of nitrogen and nitric oxide. While nitrogen is typically used to dilute the concentration of nitric oxide within the pressurized cylinder, any inert gas can also be used. When the nitric oxide gas source 8 is stored in a pressurized cylinder, it is preferable that the concentration of nitric oxide in the pressurized cylinder fall within the range of about 1 ppm to about 200,000 ppm or higher. In certain settings, extremely high concentrations of nitric oxide may be undesirable because unintentional leakage of nitric oxide gas may be more hazardous. Pressurized cylinders containing low concentrations of nitric oxide (i.e., less than 1000 ppm nitric oxide) can also be used in accordance the device and method disclosed herein. Of course, the lower the concentration of nitric oxide used, the more often the pressurized cylinders will need replacement.

FIG. 1 also shows the source of an optional dilutent gas 14 as part of the nitric oxide delivery device 2 that is used to dilute the concentration of nitric oxide. The source of dilutent gas 14 can contain nitrogen, air, oxygen, an inert gas, or a mixture of these gases. The source of dilutent gas 14 is shown as being stored within a pressurized cylinder. While the use of a pressurized cylinder is shown in FIG. 1 as the means for storing the source of dilutent gas 14, other storage and delivery means, such as a dedicated feed line (wall supply), or air pump, can also be used.

The nitric oxide gas from the nitric oxide gas source 8 and the optional dilutent gas from the dilutent gas source 14 preferably pass through pressure regulators 16 to adjust the pressure of gas that is admitted to the gas delivery device 2 to the appropriated desired pressure and the appropriate desired concentration. The respective gas streams pass via tubing 18 to an optional gas blender 20. The gas blender 20 mixes the nitric oxide gas, and the optional dilutent gas to produce a nitric oxide gas mixture that has the desired concentrations of nitric oxide. In various embodiments, the gas mixture that is output from the gas blender 20 has a concentration of nitric oxide that ranges from about 1 ppm to about 40,000 ppm. In various embodiments, the gas mixture that is output from the gas blender 20 has a concentration of nitric oxide that ranges from about 1 to about 1500 ppm, from about 1000 to about 5000 ppm, from about 4000 to about 10,000 ppm, from about 9,000 to about 16,000 ppm, from about 15,000 to about 22,000 ppm, from about 21,000 to about 28,000 ppm, from about 27,000 to about 34,000 ppm, and from about 33,000 to about 40,000 ppm. Preferably, the gas mixture that is output from the gas blender 20 has a concentration of nitric oxide that is about 30,000 ppm. Even more preferably, the concentration of nitric oxide in the gas mixture that is output from the gas blender 20 is about 20,000 ppm nitric oxide. Even more preferably, the concentration of nitric oxide in the gas mixture that is output from the gas blender 20 is about 10,000 ppm nitric oxide. In an aspect, the nitric oxide concentration in the gas mixture used for treatment can fall in the range of 1000 ppm to 40,000 ppm. For a given application, the concentration of nitric oxide selected, as well as the exposure time selected, will vary according to a variety of circumstances including, for example, the particular treatment site, and/or the particular disorder being treated. By way of a non-limiting example, a higher concentration of nitric oxide may be used when a shorter treatment time is desired. By way of other non-limiting examples, a high concentration of nitric oxide could be applied for a relatively short time (e.g., 10,000 ppm for 30 minutes or 30,000 ppm for 20 minutes). By way of another non-limiting example, a low concentration of nitric oxide could be applied for a relatively long time (e.g., 1000 ppm for 8 hours). In one embodiment, the concentration of applied nitric oxide could be kept constant for the entire exposure time. In another embodiment, the concentration of applied nitric oxide is adjusted during the exposure time. For example, by way of a non-limiting example, 200 ppm nitric oxide could be applied for 2 hours and then 20 ppm nitric oxide could be applied for an additional 3 hours. In a particular embodiment, the concentration of applied nitric oxide could be changed during the exposure at least 2 times, or 3 times, or 4 times, or 5 times, or 10 times, etc. Moreover, a particular site may be treated only once, or a particular site may be treated repeatedly over a period of days or weeks, at a constant concentration or at various concentrations. Based on the disclosure set forth herein, the skilled artisan will understand how to adjust the concentration of nitric oxide, and moreover, how to select the concentration of nitric oxide necessary for any particular application. However, it will be understood that the present application also teaches the skilled artisan how to determine the concentration of nitric oxide, and the concentration of oxygen, useful for any particular set of circumstances, based on the time of treatment and also based on the desired outcome of the treatment (e.g., alleviation of symptoms versus eradication of the disorder).

The gas mixture containing nitric oxide that is output from the gas blender 20 travels via tubing 18 to a flow control valve 22. The flow control valve 22 can include, for example, a proportional control valve that opens (or closes) in a progressively increasing (or decreasing if closing) manner. As another example, the flow control valve 22 can include a mass flow controller. The flow control valve 22 controls the flow rate of the gas mixture that is input to the bathing unit 6. The gas mixture leaves the flow control valve 22 via flexible tubing 24. The flexible tubing 24 attaches to an inlet 26 in the bathing unit 6. The inlet 26 might include an optional one way valve 64 (see FIG. 3) that prevents the backflow of the gas mixture into the tubing 24.

Still referring to FIG. 1, the bathing unit 6 is shown connected to the surface of a subject 4. Although FIG. 1 depicts a bathing unit 6 connected to the surface of the mid-region of a subject 4, it should be understood that the bathing unit 6 can be modified as appropriate to bathe any treatment site on the surface of, or inside the body of, a subject. The treatment area 30 which can be skin, tissue, an abscess, lesion, wound, surgical site, apparently intact tissue, burn, or the like, is enclosed by the bathing unit 6. The bathing unit 6 optionally includes a seal portion 32, which can be used to form a seal with subject 4. In some embodiments, the optional seal portion 32 can be used to form a substantially air-tight seal to diminish the amount of nitric oxide-containing gas that leaks out of the bathing unit 6 (e.g., no more than about 5% of the nitric oxide-containing gas delivered to the bathing unit 6). In other embodiments, the optional seal portion 32 forms a seal that is not an air-tight seal and nitric oxide-containing gas can leak out of the bathing unit. The seal portion 32 may comprise an inflatable seal 61, such as that shown in FIG. 2 and FIG. 3, or alternatively the seal portion 32 may comprise a flexible skirt or the like that conforms to the surface of the subject 4. The seal portion 32 also might include an adhesive portion that adheres to the surface of a subject 4. In other various embodiments, the seal portion 32 may merely comprise the interface of the bathing unit 6 with the subject 4.

Figure 5:
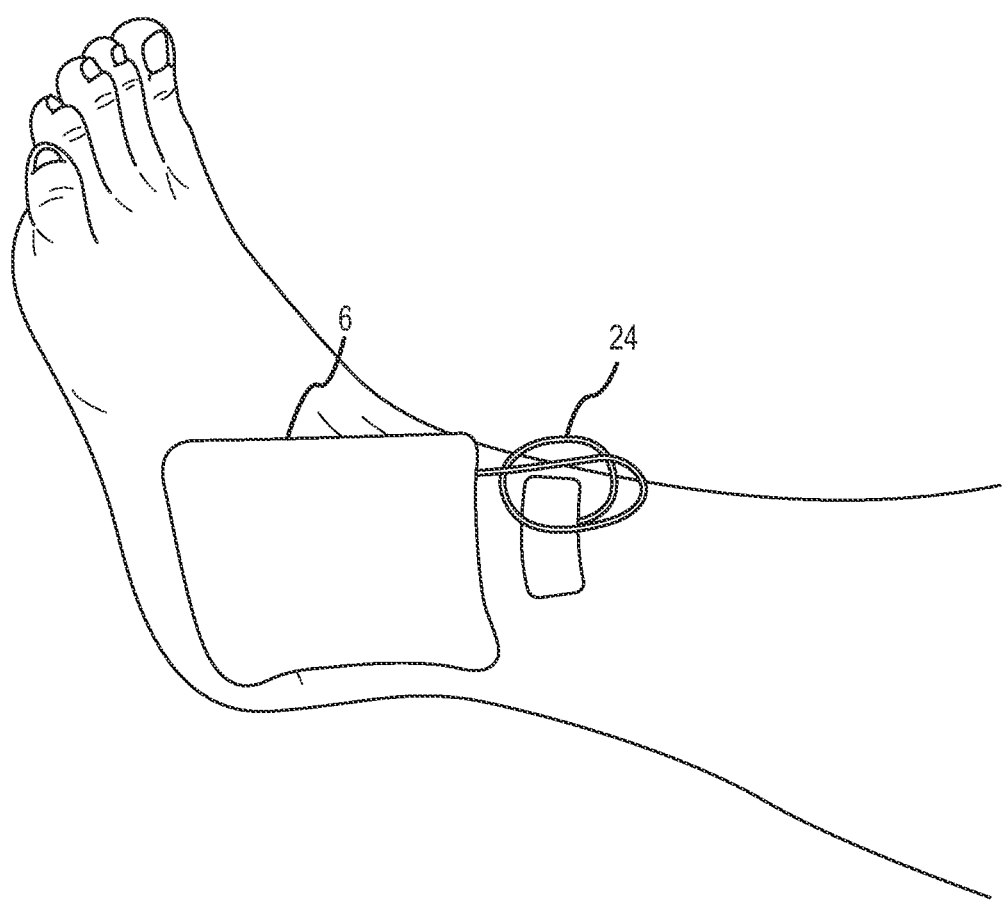
FIG. 5 depicts an image of a local wound cover bathing unit that uses just a single tube to flow the gas into the bathing unit and allows the gas to exit through one or more holes in the top occlusive cover.
Figure 6:
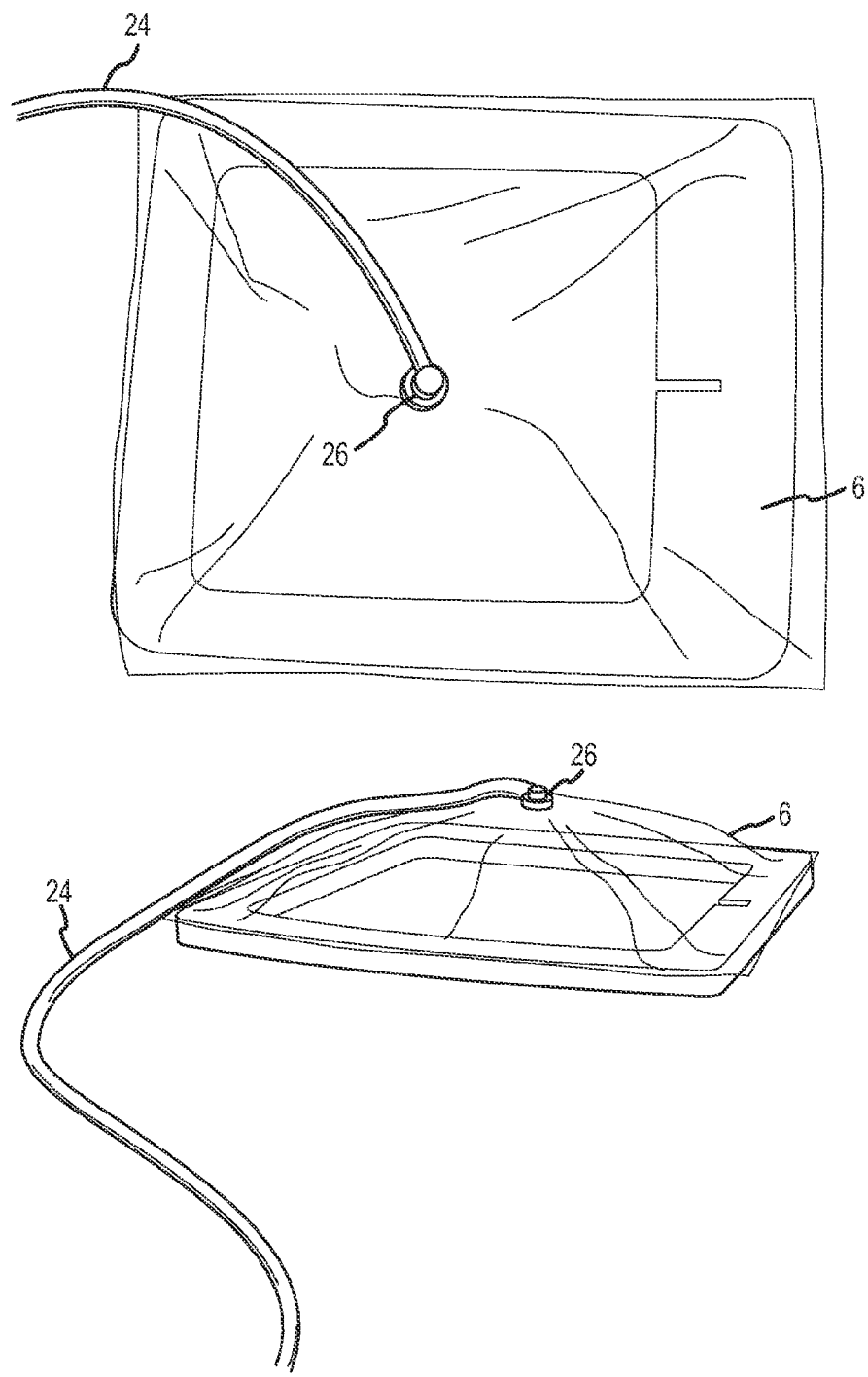
FIG. 6 depicts an image of a bathing unit that uses a single tube to flow the gas into the bathing unit, the top portion of which is raised above the treatment surface.

The bathing unit 6 can be made of a virtually limitless number of shapes and materials depending on its intended use. The bathing unit 6 might be formed as a rigid structure, such as that depicted in FIG. 1, that is placed over the treatment area 30. Alternatively, the bathing unit 6 can be formed of a flexible, bag-like material that is inflatable over the treatment area 30. FIG. 2 shows such a structure in the shape of a boot that is placed over the subject's 4 foot. FIG. 3 shows another inflatable bathing unit 6 that is formed in the shape of a mitten or glove that is worn over the subject's 4 hand. FIG. 5 depicts an image of an example local wound cover bathing unit 6 that uses a single tube 24 to flow the gas into the bathing unit and allows the gas to exit through one or more holes in the top occlusive cover. FIG. 6 depicts an image of an example bathing unit 6 that uses a single tube 24 to flow the gas into 26 the bathing unit, the top portion of which is raised above the treatment surface.

In a preferred embodiment of the invention, bathing unit 6 is constructed to hold gaseous nitric oxide mixtures at a pressure greater than 1 atm. In one embodiment, flow control valve 22 controls the flow of gas into bathing unit 6 such that the gaseous mixture exists at a pressure greater than 1 atm within bathing unit 6. In various embodiments, the pressure of the gas mixture within bathing unit 6 ranges from about 1.1 atm to about 3.5 atm. In various embodiments, the pressure of the gas mixture within bathing unit 6 ranges from about 1.1 to about 3.0 atm, from about 1.1 to about 2.0 atm, from about 1.1 to about 1.8 atm, from about 1.1 to about 1.6 atm, from about 1.1 to about 1.5 atm, from about 1.1 to about 1.4 atm, and from about 1.1 to about 1.3 atm. Preferably, the pressure of the gas mixture within bathing unit 6 is about 1.2 atm. Even more preferably, the pressure of the gas mixture within bathing unit 6 is about 1.5 atm. Even more preferably, the pressure of the gas mixture within bathing unit 6 is about 1.8 atm. Based on the disclosure set forth herein, the skilled artisan will understand how to adjust the pressure of the nitric oxide mixture, and moreover, how to select the pressure of the nitric oxide mixture necessary for any particular application. However, it will be understood that the present application also teaches the skilled artisan how to determine the pressure of the nitric oxide mixture, useful for any particular set of circumstances, based on the time of treatment and also based on the desired outcome of the treatment. Control of the pressure at which nitric oxide mixture is delivered to a treatment site may occur at various aspects of the delivery device. For example, in one embodiment, pressure of the nitric oxide mixture at the treatment site is regulated by the flow rate of nitric oxide gas mixture to the bathing unit. Alternatively, pressure of the nitric oxide mixture at the treatment site is regulated by the flow of gas out of the bathing unit applied to the treatment site. The devices described herein can contain a substantially air-tight seal that allows for a build-up of pressure to greater than about 1 atm. Such embodiments can be further modified to have a regulator or valve, such as for example a pop-off valve, on the effluent path that can allow for the selection of a pressure greater than about 1 atm. In one embodiment, delivery of nitric oxide at a pressure greater than 1 atm is achieved by utilizing a hyperbaric chamber to surround the treatment area, and/or the entire subject.

In a preferred embodiment of the invention, the bathing unit 6 includes a sensor 34 that measures the concentration of nitric oxide gas and the pressure of the gaseous mixture within the bathing unit 6. The nitric oxide sensor 34 preferably reports this information to a controller 36 via signal line 38. An optional nitric dioxide sensor 40 can also be included within the bathing unit 6. The nitric dioxide sensor 40 preferably reports the concentration of nitric dioxide to the controller 36 via signal line 42. The sensors 40, 42 can be a chemilluminesence-type, electrochemical cell-type, or spectrophotometric-type sensor.

The bathing unit 6 also includes an outlet 44 that can be used to allow the gas mixture to exit the bathing unit 6. The outlet 44 is preferably located away from the gas inlet 26 such that gas mixture does not quickly enter and exit the bathing unit 6. Preferably, the inlet 26 and outlet 44 are located in areas of the bathing unit 6 such that the gas mixture has a relatively long residence time. Flexible tubing 46 is connected to the outlet 44 and provides a conduit for the removal of gases from the bathing unit 6.

In another preferred embodiment of the invention, the flexible tubing 46 is in fluid communication with an absorber unit 48. The absorber unit 48 preferably absorbs, scrubs, or strips nitric oxide from the gas stream that is exhausted from the bathing unit 6. It is also preferable for the absorber unit 48 to also absorb, scrub, or strip nitric dioxide from the gas stream that is exhausted from the bathing unit 6. Since these gases are toxic at high levels when inhaled, it is preferable that these components are removed from the delivery device 2 prior to the gas being vented to the atmosphere. In addition, these gases can react with the internal components of the optional vacuum unit 10 and potentially interfere with the operation of the delivery device 2.

The now clean gas travels from the absorbing unit 48 to an optional vacuum unit 10 via tubing 50. The optional vacuum unit 10 provides a negative pressure within the tubing 50 so as to extract gases from the bathing unit 6. The optional vacuum unit 10 is preferably controllable with respect to the level of vacuum or suction supplied to the tubing 50 and bathing unit 6. In this regard, in conjunction with the flow control valve 22, the amount of nitric oxide gas within the bathing unit 6 can be regulated. Preferably, the vacuum unit 10 is coupled with the controller 36 via a signal line 52. The controller 36, as discussed below, preferably controls the level of output of the vacuum unit 10. The gas then passes from the vacuum unit 10 to a vent 54 that is open to the atmosphere.

It should be understood that the vacuum unit 10, as well as the absorbing unit 48, are optional components of the delivery device 2. The gas laden with nitric oxide and nitric dioxide does not have to be removed from the gas stream if there is no concern with local levels of nitric oxide and nitric dioxide. For example, the gas can be exhausted to the outside environment where high concentrations of nitric oxide and nitric dioxide will not develop. Alternatively, a recirculation system (not depicted in FIG. 1) might be used to recycle the gas mixture or the nitric oxide within the bathing unit 6.

Still referring to FIG. 1, the delivery device 2 preferably includes a controller 36 that is capable of controlling the flow control valve 22 and the vacuum unit 10. The controller 36 is preferably a microprocessor-based controller 36 that is connected to an input device 56. The input device 56 is used by an operator to adjust various parameters of the delivery device such as nitric oxide concentration in the mixture, residence time of nitric oxide, pressure within the bathing unit 6, etc. An optional display 58 can also be connected with the controller 36 to display measured parameters and settings such as the set-point nitric oxide concentration, the concentration of nitric oxide within the bathing unit 6, the concentration of nitric dioxide within the bathing unit 6, the flow rate of gas into the bathing unit 6, the flow rate of gas out of the bathing unit 6, the total time of delivery, the pressure within the bathing unit, and the like.

The controller 36 preferably receives signals from sensors 34, 40 regarding gas concentrations and pressure if such sensors 34, 40 are present within the delivery device 2. Signal lines 60, 52 are connected to the flow control valve 22 and vacuum unit 10 respectively for the delivery and receipt of control signals.

In another embodiment of the invention, the controller 36 is eliminated entirely. In this regard, the flow rate of the gas into the bathing unit 6 and the flow rate of the gas out of the bathing unit 6 are pre-set or adjusted manually. For example, an operator can set a vacuum output that is substantially equal to the flow rate of the gas delivered to the bathing unit 6 via the flow control valve 22. In this manner, nitric oxide gas will be able to bathe the infected area 30 without any build-up or leaking of nitric oxide or nitric dioxide gas from the delivery device 2.

Figure 4:
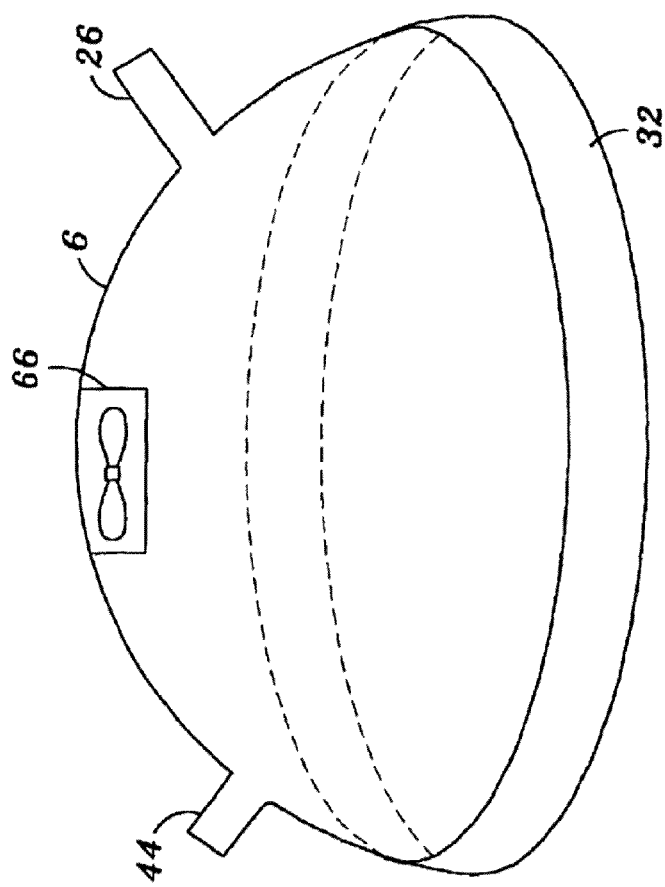
FIG. 4 depicts a bathing unit including an agitator located therein.

FIG. 2 illustrates a bathing unit 6 in the shape of a boot that is used to treat an infected area 30 located on the leg of the subject 4. The bathing unit 6 includes an inflatable seal 61 that surrounds the leg region to make a seal with the surface of the subject 4. This embodiment shows a nozzle 62 that is affixed near the inlet 26 of the bathing unit 6. The nozzle 62 directs a jet of nitric oxide gas mixture, onto the treatment area 30. The jet of gaseous nitric oxide aids in penetrating the treatment area 30 with nitric oxide. FIG. 3 shows another embodiment of the bathing unit 6 in the shape of a mitten or glove. The bathing unit 6 is also inflatable and contains an inflatable seal 61 that forms a seal around the surface of the subject 4. FIG. 3 also shows an optional one way valve 64 located in the inlet 26. As seen in FIGS. 3 and 4, the inlet 26 and outlet 44 are located away from one another, and preferably on opposing sides of the treated area such that freshly delivered nitric oxide gas is not prematurely withdrawn from the bathing unit 6.

For treatment of a treatment area 30, the bathing unit 6 is placed over the treatment area 30. A seal is then formed between the surface of the subject 4 and the bathing unit 6. If the bathing unit 6 has an inflatable construction, the bathing unit 6 must be inflated with gas. Preferably, the bathing unit 6 is initially inflated only with the dilutent gas to prevent the leaking of nitric oxide and nitric dioxide from the device 2. Once an adequate seal has been established, the operator of the device initiates the flow of nitric oxide from the nitric oxide gas source 8 to the bathing unit 6. As described above, this may be accomplished manually or via the controller 36. The skilled artisan will know how to establish the appropriate seal—either air-tight, or less than air-tight (e.g., "free-flowing")—depending upon the particular objective and goal for treatment under any particular set of facts.

Once the bathing unit 6 has started to fill with nitric oxide gas, the optional vacuum unit 10 can be turned on and adjusted to the appropriate output level. For an inflatable bathing unit 6, the output level (i.e., flow rate) of the vacuum unit 10 should be less than or equal to the flow rate of nitric oxide gas entering the bathing unit 6 to avoid deflating the bathing unit 6 and/or to allow the pressure in the bathing unit 6 to increase. In the preferred embodiment, the pressure within bathing unit 6 is controlled to be at a pressure greater than about 1 atm. In some embodiments, the vacuum unit 10 can be set to withdraw gas at a substantially equal rate as the gas is delivered to the bathing unit 6. An effective amount of nitric oxide is delivered to the bathing unit 6, such that the pressure in the bathing unit 6 is at least about 1 atm to treat the treatment area 30. As described elsewhere herein, gaseous nitric oxide delivered at a pressure greater than about 1 atm using the devices and methods of the invention may be used to a wide range of treatment areas of a subject. Such treatment areas include but are not limited to sites of bacterial infection, fungal infection, viral infection, protozoan infection, burns, wounds, wrinkles, lesions. Other treatment areas include areas associated with inflammatory disease or surface areas where the underlying tissue is in need of enhanced blood flow or angiogenesis.

FIG. 4 shows another embodiment of the invention in which the bathing unit 6 includes an agitator 66 that is used to create turbulent conditions inside the bathing unit 6. The agitator 66 preferably is a fan-type of mechanism but can include other means of creating turbulent conditions within the bathing unit 6. The agitator 66 aids in refreshing the affected area 30 with a fresh supply of gas containing nitric oxide.

FIG. 5 illustrates another embodiment of the invention, in which the bathing unit 6 comprises a wound cover that has one or more openings for the release of nitric oxide gas. In an embodiment, nitric oxide gas is introduced 24 underneath the bathing unit, such that the gaseous nitric oxide is largely contained beneath the unit at pressures greater than about 1 atm, in a space between the unit and the surface of the subject. However, the nitric oxide gas and spent nitric oxide gas are free to escape through the one or more openings in the bathing unit. FIG. 6 illustrates another embodiment of the invention, in which the bathing unit 6 comprises a wound cover, the top portion of which is raised above the treatment surface.

As will be understood by the skilled artisan, when armed with the present disclosure, variations in the number and/or size of the openings in such a bathing unit can be used to regulate the pressure of nitric oxide gas underneath the wound cover, and/or to regulate the amount of time that the gaseous nitric oxide is in contact with the a treatment site beneath the wound cover. It will also be understood that in any method or apparatus of the invention, the nitric oxide gas that is delivered to a subject may optionally be evacuated after use. The skilled artisan will understand, when armed with the disclosure set forth herein, how to determine the timing and method of evacuation.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Antimicrobial Activity of Nitric Oxide Delivered at a Pressure Greater than 1 atm An experiment is conducted to evaluate the antimicrobial activity of nitric oxide delivered at a pressure greater than 1 atm, as compared with the antimicrobial activity of nitric oxide delivered at pressures at 1 atm. Full-thickness porcine wounds are infected with bacteria, and then treated with nitric oxide at a pressure greater than 1 atm or at 1 atm. Infected wounds are treated with either 10,000 ppm nitric oxide delivered at 1 atm for 30 minutes, or 10,000 ppm nitric oxide delivered at a pressure greater than 1 atm for 10-120 minutes. After treatment, biopsies of infected and treated wounds, as well as of infected but untreated wounds, are taken and a bacterial population count from each biopsy is determined.

A pathogen-free, commercially-raised, female, Yorkshire-cross pig weighing about 20 to 30 kg (Real Hog Farm, Marion, Tex.) is used. Before and during therapy, the pig is housed in a raised stainless steel pen cage (6'×6'). The pig is fed antibiotic-free feed (Lab Diet Mini-Pig HF grower, PMI Nutrition International Inc., Brentwood, Mo.) and is provided tap water ad libitum. Prior to wound creation, the pig receives a comprehensive health inspection. Also, 24 hours post wound infection, and just prior to the nitric oxide treatments, the general health and appearance of the pig is again monitored.

The day before wound creation, the pig is anesthetized with Telazol (Tiletamine/Zolazepam; 5 mg/kg, intramuscular; Fort Dodge Animal Health, Fort Dodge, Iowa). A small portion of the caudal dorsum is trimmed with a #40 Oster clipper blade. A Fentanyl patch, Duragesic (2.5 µg/hr) (Fentanyl transdermal system, Watson Laboratories, Inc., Corona, Calif.), is secured to the shaved skin as post-surgical pain management. The pig is premedicated by intramuscular injection of Glycopyrrolate (0.003 mg/kg) (American Regent Inc., Shirley, N.Y.) follow by Telazol (Tiletamine/Zolazepam; 5 mg/kg intramuscular; Fort Dodge Animal Health, Fort Dodge, Iowa) and followed by intubation and inhalation of 1 to 2 percent Isoflurane USP (Attane, Minrad Inc., Buffalo, N.Y.) mixed with oxygen. The dorsal and lateral thorax and abdomen of the pig is trimmed with a #40 Oster clipper blade and washed with an antimicrobial-free soap.

On the day of wound creation (Day 0), the pig is transferred to a surgical suite and general anesthesia is continued. Blood is drawn immediately prior to wound creation and is streaked on Tryptic Soy Broth (TSB), *Pseudomonas* Isolation Agar (PIA) and Mannitol Salts Agar (MSA) agar plates, to assess for the presence of bacteria in the blood.

Sixteen full-thickness wounds, each about 20 mm in diameter, are created using custom-designed 2-cm trephine. Wounds are placed in groups of 4, with space left between the groups to allow for the proper later application of dressing materials. Additionally, each wound is placed so that at least about 2 cm remains between it and any other wound. See FIG. 7 for a picture depicting the arrangement of wounds.

Epinephrine solution (1:10,000 dilution) is applied using gauze sponges until hemostasis is achieved (approximately 10 minutes). The wounds are inoculated with coagulase-negative Staphylococci (CNS), which is grown in standard growth media at 37° C. overnight prior to the day of wound creation. On the morning of wound creation, the CNS, grown to a density of $10^{10}$ CFU/mL, is washed with sterile saline and resuspended in saline to a final density of approximately $10^6$ CFU/mL. Sufficient inoculum is made to ensure that all the wounds could be saturated with the same preparation. CNS solution-saturated sponges are applied to the wounds. The sponges are left on the wounds and covered with an occlusive layer of Saran Wrap (S.C. Johnson & Sons, Brantford, ON) for 15 minutes. Then, the contaminated Saran Wrap and sponges are removed and discarded. All wounds are dressed using an absorbent dressing, Telfa™ (Covidien Mansfield, Mass.). Before applying the Telfa dressings, they are moistened with saline and squeezed to remove excess saline. The Telfa dressings are secured in place with Transpore tape (3M, St. Paul, Minn.). All wounds are covered with a blue-absorbent pad as a secondary dressing. The absorbent layer of the blue pad is left in place for 24 hours. The pig is wrapped with a layer of elastic bandage over the blue pad to prevent movement of the dressings underneath. The pig is returned to its cage.

On Day 1, 24 hours after CNS inoculation, and just prior to commencing therapy, the pigs receive another health assessment. Immediately prior to commencing therapy, a second blood sample is taken and streaked on TSB, PIA and MSA agar plates to assess for the presence of bacteria in the blood. The wounds are covered with modified Hathback Dressing and bathed with gas. See arrangement of treatment/control regime in FIG. 7. Columns A & B, sites 1 & 2: 120 minutes nitric oxide, delivered at a pressure of about 1 atm. Columns C & D, sites 1 & 2: 120 minutes nitric oxide, delivered at a pressure greater than 1 atm (for example 1.1, 1.2, 1.3, 1.4, 1.5, 2.0, 2.5, 3.0 atm). Columns C & D, sites 3 & 4: 30 minutes nitric oxide, delivered at a pressure greater than 1 atm (for example 1.1, 1.2, 1.3, 1.4, 1.5, 2.0, 2.5, 3.0 atm). Columns A & B, sites 3 & 4, control, no treatment (moist dressing). Gas was delivered with a flow rate between 0.25 and 1 liter per minute.

Figure 7:
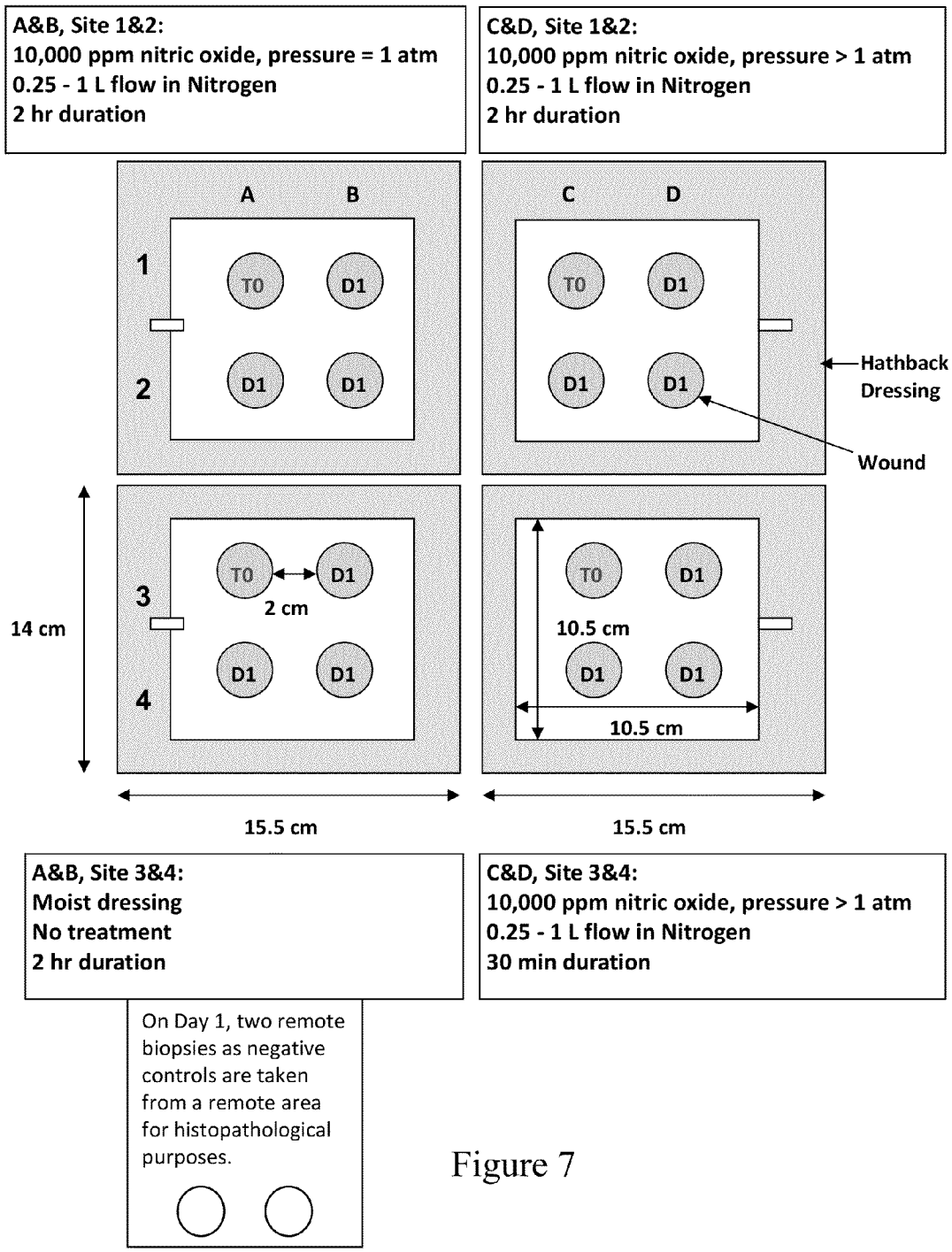
FIG. 7 depicts a drawing indicating arrangement of wounds and treatment parameters used in Experimental Example 1.

After therapy, a third blood sample is taken, immediately upon conclusion of the 2 hour treatments with NO therapy and is streaked on TSB, PIA and MSA agar plates to assess for the presence of bacteria in the blood On Day 1, twenty four hours after CNS inoculation and prior to therapy, 28 biopsies are taken; seven biopsies from each T0 wound (see FIG. 7). On Day 1 post therapy, 86 biopsies are taken, seven biopsies from each D1 wound and two biopsies from a remote area. Two biopsies are taken from inside and one from outside of each wound for microbiological sampling, and are made using a 4-mm biopsy punch. One inside biopsy is taken in the approximate center of the wound. A second inside biopsy is taken at a position of "12 o'clock" immediately inside (but not including) the wound edge. One biopsy from inside the wound and one biopsy from outside the wound is rinsed in 10% NBF to remove blood and placed in fresh for histopathology examination. Two biopsies are taken from remote areas as negative controls for histopathological purposes.

The biopsy tissues are placed into a pre-weighed vessel containing phosphate buffered saline and the weight of tissue is determined. The biopsy samples are individually homogenized and serially diluted. After processing, the pre-therapy microbiology samples are plated. The serial dilutions are Drop-Plated and incubated to determine the bacterial counts. The samples are plated on TSB to determine the total number of bacteria present in the biopsy specimen. The samples are plated on MSA to determine the number of Staphylococci present in the biopsy specimen. Bacterial counts are expressed as $\log_{10}$ (CFU/g).

After processing, the post NO therapy microbiology samples are plated at two time points: immediately after processing and two hours after processing. At t=0 hours, the serial dilutions are Drop-Plated and incubated to determine the bacterial counts. The samples are plated on TSB to determine the total number of bacteria present in the biopsy specimen. The samples are plated on MSA to determine the number of staphylococci present in the biopsy specimen. Bacterial counts are expressed as $\log_{10}$ (CFU/g). At t=2 hours, the serial dilutions are Drop-Plated following a 2-hour incubation in saline, and then incubated to determine the bacterial counts. The samples are plated on TSB to determine the total number of bacteria present in the biopsy specimen. The samples are plated on MSA to determine the number of staphylococci present in the biopsy specimen. Bacterial counts are expressed as $\log 10$ (CFU/g).

Example 2

Antimicrobial Activity of Nitric Oxide Delivered at a Pressure Greater than 1 atm Experiments are conducted to evaluate the antimicrobial activity of nitric oxide delivered at a pressure greater than 1 atm. Full-thickness porcine wounds are infected with bacteria, and then treated with nitric oxide at a pressure greater than 1 atm. Two pigs are used. For pigs 1 and 2, infected wounds are treated with either 10,000 ppm nitric oxide delivered at 1.1 atm for 30 minutes, 10,000 ppm nitric oxide in combination delivered at 1.5 atm for 30 minutes, or 10,000 ppm nitric oxide delivered at 1.8 atm for 30 minutes. After treatment, biopsies of infected and treated wounds, as well as of infected but untreated wounds, are taken and a bacterial population count from each biopsy is determined in duplicate.

Pathogen-free, commercially-raised, female, Yorkshire-cross pigs weighing about 20 to 30 kg (Real Hog Farm, Marion, Tex.) are used. Before and during therapy, the pigs are housed in a raised stainless steel pen cage (6×6'). The pigs are fed antibiotic-free feed (Lab Diet Mini-Pig HF grower, PMI Nutrition International Inc., Brentwood, Mo.) and are provided tap water ad libitum. Prior to wound creation, the pigs receive a comprehensive health inspection. Also, 24 hours post wound infection, and just prior to the nitric oxide treatments, the general health and appearance of the pigs are again monitored.

The day before wound creation, the pigs are anesthetized with Telazol (Tiletamine/Zolazepam; 5 mg/kg, intramuscular; Fort Dodge Animal Health, Fort Dodge, Iowa). A small portion of the caudal dorsum is trimmed with a #40 Oster clipper blade. A Fentanyl patch, Duragesic (2.5 ug/hr) (Fentanyl transdermal system, Watson Laboratories, Inc., Corona, Calif.), is secured to the shaved skin as post-surgical pain management. The pigs are premedicated by intramuscular injection of Glycopyrrolate (0.003 mg/kg) (American Regent Inc., Shirley, N.Y.) follow by Telazol (Tiletamine/Zolazepam; 5 mg/kg intramuscular; Fort Dodge Animal Health, Fort Dodge, Iowa) and followed by intubation and inhalation of 1 to 2 percent Isoflurane USP (Attane, Minrad Inc., Buffalo, N.Y.) mixed with oxygen. The dorsal and lateral thorax and abdomen of the pigs is trimmed with a #40 Oster clipper blade and washed with an antimicrobial-free soap.

On the day of wound creation (Day 0), the pigs are transferred to a surgical suite and general anesthesia is continued. Blood is drawn immediately prior to wound creation and streaked on TSB, PIA and MSA agar plates to assess for the presence of bacteria in the blood.

On each of the pigs, sixteen full-thickness wounds, each about 20 mm in diameter, are created using custom-designed 2-cm trephine. Wounds are placed in groups of 4, with space left between the groups to allow for the proper later application of dressing materials. Additionally, each wound is placed so that at least about 2 cm remains between it and any other wound. See FIG. 8 for a picture depicting the arrangement of wounds.

Epinephrine solution (1:10,000 dilution) is applied using gauze sponges until hemostasis is achieved (approximately 10 minutes). The wounds are inoculated with coagulase-negative Staphylococci (CNS), which is grown in standard growth media at 37° C. overnight prior to the day of wound creation. On the morning of wound creation, the CNS, grown to a density of $10^{10}$ CFU/mL, are washed with sterile saline and resuspended in saline to a final density of approximately $10^6$ CFU/mL. Sufficient inoculum is made to ensure that all the wounds could be saturated with the same preparation.

CNS solution-saturated sponges are applied to the wounds. The sponges are left on the wounds and covered with an occlusive layer of Saran Wrap (S.C. Johnson & Sons, Brantford, ON) for 15 minutes. Then, the contaminated Saran Wrap and sponges are removed and discarded. All wounds are dressed using an absorbent dressing, Telfa™ (Covidien Mansfield, Mass.). Before applying the Telfa dressings, they are moistened with saline and squeezed to remove excess saline. The Telfa dressings are secured in place with Transpore tape (3M, St. Paul, Minn.). All wounds are covered with a blue-absorbent pad as a secondary dressing. The absorbent layer of the blue pad is left in place for 24 hours. The pigs are wrapped with a layer of elastic bandage over the blue pad to prevent movement of the dressings underneath. The pigs are returned to their cages.

On Day 1, 24 hours after CNS inoculation, and just prior to commencing therapy, the pigs receive another health assessment. Immediately prior to commencing therapy, a second blood sample is taken and streaked on TSB, PIA and MSA agar plates to assess for the presence of bacteria in the blood. The wounds are covered with modified Hathback Dressing and bathed with gas. See arrangement of treatment/control regime in FIG. 8, where Columns A & B, sites 1 & 2: 30 minutes nitric oxide delivered at 1.1 atm. Columns C & D, sites 1 & 2: 30 minutes nitric oxide delivered at 1.5 atm. Columns C & D, sites 3 & 4: 30 minutes nitric oxide delivered at 1.8 atm. Columns A & B, sites 3 & 4, control, no treatment (moist dressing). Gas is delivered with a flow rate between 0.25 and 1 liter per minute.

Figure 8:
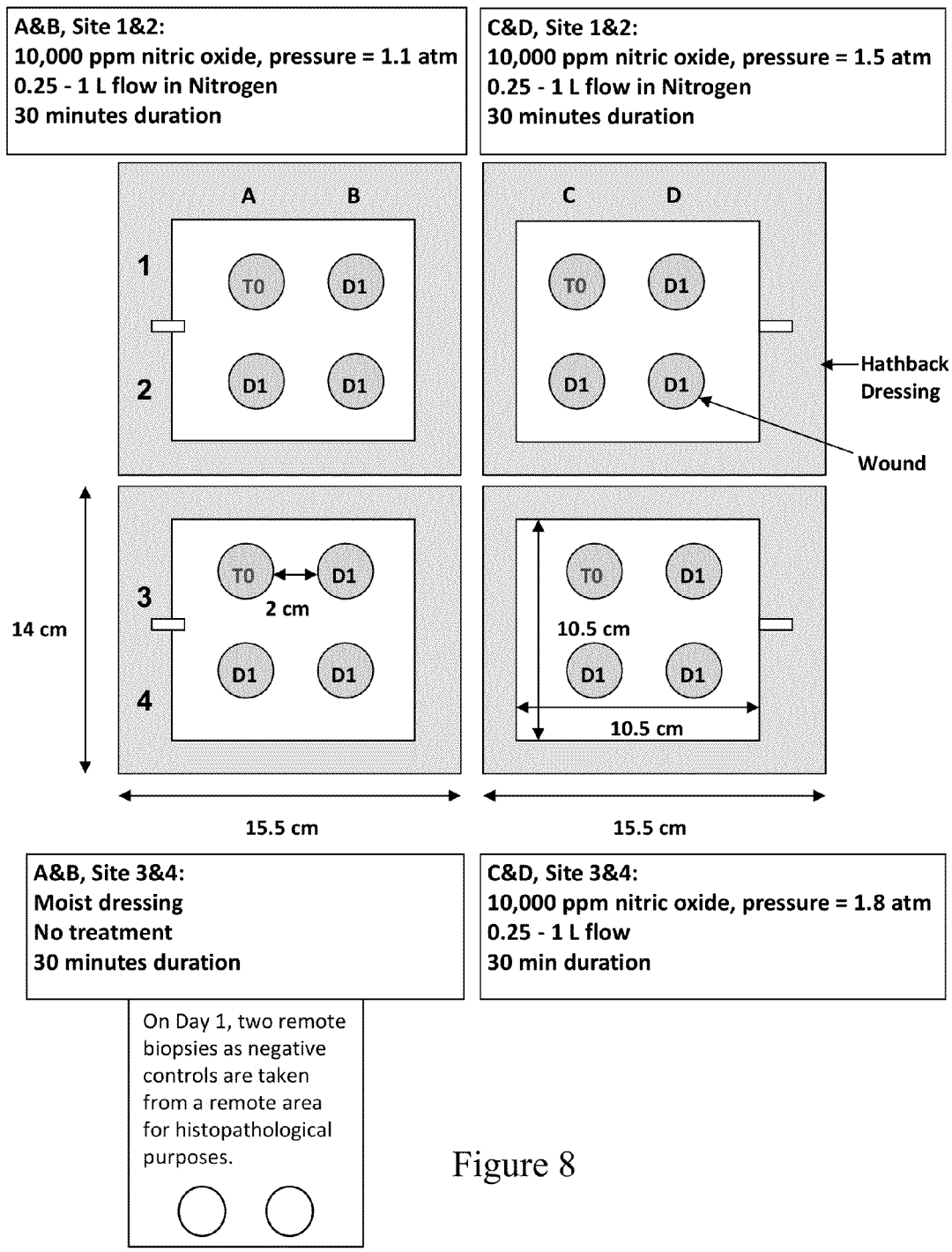
FIG. 8 depicts a drawing indicating arrangement of wounds and treatment parameters used in Experimental Example 2.

Immediately after therapy, a third blood sample is taken and streaked on TSB, PIA and MSA agar plates to assess for the presence of bacteria in the blood On Day 1, twenty four hours after CNS inoculation and prior to therapy, from each of the pigs, 28 biopsies are taken; seven biopsies from each T0 wound (see FIG. 8). On Day 1 post therapy, 86 biopsies are taken, seven biopsies from each D1 wound and two biopsies from a remote area. Two biopsies are taken from inside and one from outside of each wound for microbiological sampling, and are made using a 4-mm biopsy punch. One inside biopsy is taken in the approximate center of the wound. A second inside biopsy is taken at a position of "12 o'clock" immediately inside (but not including) the wound edge. One biopsy from inside the wound and one biopsy from outside the wound are rinsed in 10% NBF to remove blood and placed in fresh for histopathology examination. Two biopsies are taken from remote areas as negative controls for histopathological purposes.

The biopsy tissues are placed into a pre-weighed vessel containing phosphate buffered saline and the weight of tissue is determined. The biopsy samples are individually homogenized and serially diluted. After processing, each serial dilution is Drop-Plated and incubated on two separate Tryptic Soy Agar (TSA) plates to determine the bacterial count. Bacterial counts are expressed as $\log_{10}$ (CFU/g).

Example 3

Figure 9:
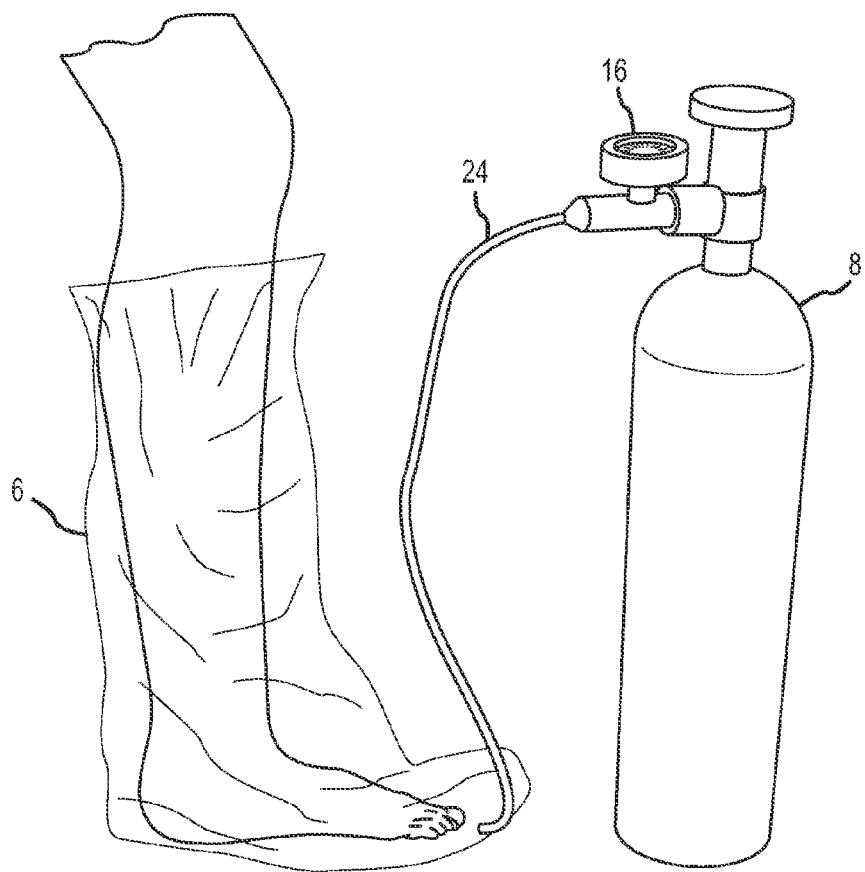
FIG. 9 depicts an example device for the delivery of nitric oxide containing gas to the foot of a subject with tinea pedis.

Treatment of Mild Tinea Pedis by Delivery of Nitric Oxide at a Pressure Greater than 1 atm To evaluate the effectiveness of gaseous nitric oxide treatment, delivered at a pressure greater than 1 atm, against mild tinea pedis, a single-site clinical trial treating 10 human subjects with mild tinea pedis is conducted. Subjects who had a pre-existing chronic systemic dermal disease, other than tinea in, or immediately around the area under evaluation are excluded from this study. The foot of each subject is fitted with a flexible, plastic boot-like enclosure that is sealed at the mid-calf 6 (see, for example, FIG. 9) and the foot is bathed 24 with 1% gaseous nitric oxide 8 in nitrogen at a pressure greater than 1 atm (e.g., 1.1-1.9 atm) and at a fixed flow 16 of 1 liter per minute for a total of 2 hours divided over 5 treatment days. Gas enters the boot-like enclosure near the toe region with passive diffusion from the enclosure into a well-ventilated examination room. On day 1, subjects are treated for 10 minutes. On day 2, subjects are treated for 20 minutes. On each of days 3, 4 and 5, subjects are treated for 30 minutes. On days 0, 1, 2, 3, 4, 5 and 12, each subject is assessed by a podiatrist blinded to the subject's treatment group and is given a clinical symptom severity score ranging from 0 to 64. The clinical symptom severity score is determined by scoring each of 8 categories (i.e., fissures/cracks, yellow crusting (ruptured blisters), maceration (white moist skin), pruritus (itching), scaling, erythema, vesicles/blisters and burning) on an 8-point scale (i.e., 0=absent, 1-2 mild, 3-5 moderate and 6-8 severe).

Example 4

Treatment of Moderate-Severe Interdigital and/or Moccasin-Type Tinea Pedis by Delivery of Nitric Oxide at a Pressure Greater than 1 atm To evaluate the effectiveness of gaseous nitric oxide treatment, delivered at a pressure greater than 1 atm, against moderate-severe interdigital and/or moccasin-type tinea pedis, a single-site, placebo-controlled clinical trial treating ≥50 evaluable human subjects with moderate-severe interdigital tinea pedis is conducted. Subjects who had a pre-existing chronic systemic dermal disease, other than tinea in, or immediately around the area under evaluation are excluded from this study. The foot of each subject is fitted with a flexible, plastic boot-like enclosure 6 that is sealed at the mid-calf (see, for example, FIG. 9) and the foot is bathed 24 with 1% gaseous nitric oxide 8 in nitrogen at a pressure of 1 atm, or 1% gaseous nitric oxide in nitrogen at a pressure greater than 1 atm (e.g., 1.1-1.9 atm), or placebo (i.e., nitrogen) at a fixed flow of 1 liter 16 per minute for 40 minutes each day for each of three consecutive days. Gas enters the boot-like enclosure 6 near the toe region with passive diffusion from the enclosure into a well-ventilated examination room. Each foot of each subject is fitted with an air-tight, ankle-high covering. On days 1, 3 and 12, each subject is assessed by a podiatrist blinded to the subject's treatment group and is given a clinical symptom severity score ranging from 0 to 64. The clinical symptom severity score was determined by scoring each of 8 categories (i.e., fissures/cracks, yellow crusting (ruptured blisters), maceration (white moist skin), pruritus (itching), scaling, erythema, vesicles/blisters and burning) on an 8-point scale (i.e., 0=absent, 1-2 mild, 3-5 moderate and 6-8 severe).

Example 5

Percutaneous Absorption of Nitric Oxide Delivered at a Pressure Greater than 1 atm The percutaneous absorption of nitric oxide is evaluated using a Franz human skin finite dose model. The in vitro Franz human skin finite dose model has proven to be a valuable tool for the study of percutaneous absorption and the determination of the pharmacokinetics of topically applied drugs. The model uses human ex vivo cadaver or surgical skin mounted in a specially designed diffusion chamber allowing the skin to be maintained at a temperature and humidity that match typical in vivo conditions. A finite dose of a formulation is applied to the outer surface of the skin and drug absorption is measured by monitoring its rate of appearance in the reservoir solution bathing the inner surface of the skin. In this study, the applied dose is a controlled continuous exposure to a gas. Data defining total absorption, rate of absorption, as well as skin content can be accurately determined in this model. The method has historic precedent for accurately predicting in vivo percutaneous absorption kinetics (Franz, 1978, Skin. Drug Application and Evaluation of Environmental Hazards, Current Problems in Dermatology, vol. 7, G. Simon, Z. Paster, M. Klingberg, M. Kaye (Eds), Basel, Switzerland, S. Karger, 1978, pp 58-68).

A single center, open label study of nitric oxide formulations is performed. The formulations are tested in triplicate on at least one skin donors using the in vitro Franz finite dose skin model (see Franz, 1975, Percutaneous absorption: on the relevance of in vitro data. J Invest Derm 64:190-195). The rate and extent of penetration of nitric oxide, at normal pressure and at greater than 1 atm of pressure (e.g., 1.2×, 1.5×, 1.8×, 2.0×, 2.2×, etc.) for continuous exposure durations of 30 and 60 minutes is determined for the amount penetrating through the skin and into the different layers of the skin using a Franz Diffusion Cell.

Human cadaver trunk skin is used in this study. It is dermatomed, cryopreserved, sealed in a water-impermeable plastic bag, and stored at −70° C. until the day of the experiment. Prior to use it is thawed in 37° C. water, then rinsed in tap water to remove any adherent blood or other material from the surface.

Skin from a single donor is cut into multiple smaller sections large enough to fit on, for example, a 1.0 cm$^2$ Franz diffusion cell. To assure the integrity of each skin section, its permeability to tritiated water is determined before application of the test products (Franz and Lehman, 1990, Abst. J Invest Dermatol 1990, 94:525). Following a brief (0.5-1 hour) equilibrium period, $^3H_2O$ (NEN, Boston, Mass., sp. Act.—0.5 pCi/mL) is layered across the top of the skin by dropper so that the entire exposed surface is covered (approximately 200-500 gL). After 5 minutes, the $^3H_2O$ aqueous layer is removed. At 30 minutes, the reservoir solution is collected and analyzed for radioactive content by liquid scintillation counting. Skin specimens in which absorption of $^3H_2O$ is less than 1 56 pi, equ/cm$^2$ are considered acceptable.

The dermal chamber is filled to capacity with a reservoir solution of phosphate-buffered isotonic saline (PBS), pH 7.4±0.1, and the epidermal chamber is left open to ambient laboratory environment. The cells are placed in a diffusion apparatus in which the dermal reservoir solution is stirred magnetically at 600 RPM and its temperature maintained to achieve a skin surface temperature of 32.0±1.0° C. The formulations are tested and the rate and extent of penetration of nitric oxide, at normal pressure and at greater than 1 atm of pressure (e.g., 1.2×, 1.5×, 1.8×, 2.0×, 2.2×, etc.) for continuous exposure durations of 30 and 60 minutes is determined for the amount penetrating through the skin and into the different layers of the skin using a Franz Diffusion Cell. Pharmacokinetic sampling of the reservoir solution occurs prior to dosing (0 hour) and, for example, at 10, 15, 30, 60 and 120 minutes during and following gas exposure. At the end of the dose duration, and following the collection of the last receptor solution, the surface of the skin sections are washed and the stratum corneum, epidermis, and dermis are isolated and each are retained for analysis. Nitric oxide concentrations are measured using an analytical method.

Figure 10:
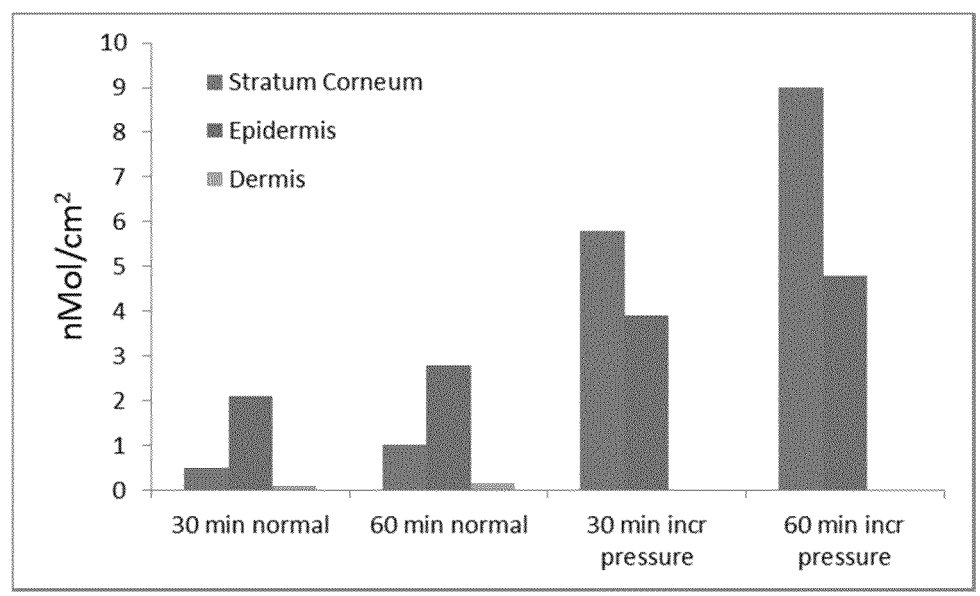
FIG. 10 depicts the results of an example experiment demonstrating that NO penetration is increased in the epidermis and stratum corneum when delivered at a pressure of 1.2 atm as compared with normal pressure.

It was observed that NO penetration was increased in the epidermis and stratum corneum, when delivered at a pressure of 1.2 atm as compared with normal pressure (FIG. 10). This data demonstrates that increasing pressure drives NO into the epidermis and stratum corneum.

Example 6

Lice

The ability of nitric oxide or nitric oxide at a pressure greater than 1 atm to kill human head louse females and eggs is evaluated using gas chamber bioassay. Human head lice from the permethrin(kdr)-resistant SF-HL strain are used in a nitric oxide gas bioassay to determine louse mortality at different exposure intervals and pressures. Adult female lice and aged eggs (6-8 day old) are used in all bioassays. The lice or eggs are placed in the bottom of a sterile disposable Petri dishes (60×20 mm) and left uncovered. The dish with lice or eggs is placed inside a polyethylene bag and the bag is taped shut with HY-TAPE® (HY-TAPE Intl., Patterson, N.Y.) to seal the chamber and to minimize the volume of gas inside the chamber. The treatments used are either nitric oxide at a final concentration of 10,000 ppm nitric oxide at a pressure greater than 1 atm, or a treatment with nitric oxide at 10,000 ppm at a pressure of 1 atm, both with a flow rate of 1 liter/minute. The gas tank is connected to the chamber with PVC tubing and plastic connectors. The chamber outlet is also connected with PVC tubing and is fed to a NO scrubber to trap the NO gas leaving the chamber. Additionally, tufts of human hair (blond and brown) are placed inside the chamber for a 30 minute exposure interval to nitric oxide to assess discoloration of the hair for cosmetic purposes.

Example 7

Wrinkles

To evaluate the effectiveness of gaseous nitric oxide treatment, delivered at a pressure greater than 1 atm, to reduce wrinkles, a single-site, placebo-controlled clinical trial treating 50 evaluable human subjects with wrinkles is conducted. A limb of each subject, which has a considerable level of wrinkles, is fitted with a sealable flexible plastic enclosure and the limb is bathed with 1% gaseous nitric oxide in nitrogen at a pressure of 1 atm or at a pressure greater than 1 atm and at a fixed flow of 1 liter per minute for a total of 2 hours divided over 5 treatment days. Gas enters the enclosure through an inlet and exits the enclosure with passive diffusion from the enclosure into a well-ventilated examination room. On day 1, subjects are treated for 10 minutes. On day 2, subjects are treated for 20 minutes. On each of days 3, 4 and 5, subjects are treated for 30 minutes. On days 0, 1, 2, 3, 4, 5 and 12, each subject is assessed by a dermatologist blinded to the subject's treatment group and each subject is given a clinical score relating to the level of wrinkle reduction as afforded by the treatment.

Example 8

Enhanced Blood Flow

To evaluate the effectiveness of gaseous nitric oxide treatment, delivered at a pressure greater than 1 atm, to enhance blood flow, a single-site, placebo-controlled clinical trial treating evaluable human subjects with critical limb ischemia (CLI) is conducted. An affected limb of each subject is fitted with a sealable flexible plastic enclosure and the limb is bathed with 1% gaseous nitric oxide in nitrogen at a pressure of 1 atm or at a pressure greater than 1 atm and at a fixed flow of 1 liter per minute for a total of 2 hours divided over 5 treatment days. Gas enters the enclosure through an inlet and exits the enclosure with passive diffusion from the enclosure into a well-ventilated examination room. On day 1, subjects are treated for 10 minutes. On day 2, subjects are treated for 20 minutes. On each of days 3, 4 and 5, subjects are treated for 30 minutes. On days 0, 1, 2, 3, 4, 5 and 12, the blood flow in the treated limb of each subject is assessed by a clinician blinded to the subject's treatment group. Blood flow is assessed using auscultation, Doppler ultrasound, CT angiography, MR angiography, and/or an angiogram.

Example 9

Inflammation

To evaluate the effectiveness of gaseous nitric oxide treatment, delivered at a pressure greater than 1 atm, to treat inflammation, a single-site, placebo-controlled clinical trial treating 50 evaluable human subjects with psoriasis is conducted. An affected limb of each subject, whereby the skin of the affected limb contains a rash indicative of psoriasis, is fitted with a sealable flexible plastic enclosure and the limb is bathed with 1% gaseous nitric oxide in nitrogen at a pressure of 1 atm or at a pressure greater than 1 atm and at a fixed flow of 1 liter per minute for a total of 2 hours divided over 5 treatment days. Gas enters the enclosure through an inlet and exits the enclosure with passive diffusion from the enclosure into a well-ventilated examination room. On day 1, subjects are treated for 10 minutes. On day 2, subjects are treated for 20 minutes. On each of days 3, 4 and 5, subjects are treated for 30 minutes. On days 0, 1, 2, 3, 4, 5 and 12, each subject is assessed by a dermatologist blinded to the subject's treatment group and each subject is given a clinical score relating to the level of improvement observed in the subject's rash.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of delivering a gas mixture containing an effective amount of nitric oxide to a treatment site of a subject comprising:
   providing a flow-controlled source of the gas mixture containing nitric oxide;
   providing a bathing unit around the skin surface of the subject, the bathing unit forming a seal with the skin surface of the subject, wherein the treatment site is at or beneath the skin surface of the subject; and
   transporting the gas mixture to the bathing unit so as to bathe the treatment site of the subject with the gas mixture at a pressure greater than 1 atmosphere.

2. The method of claim 1, further comprising refreshing the treatment site with a fresh supply of the gas mixture.

3. The method of claim 1, further comprising monitoring concentration of one or more of nitric oxide and nitric dioxide, bathing the treatment site.

4. The method of claim 1, further comprising evacuating the gas mixture from the treatment site.

5. The method of claim 1, further comprising evacuating the gas mixture from the treatment site at a flow rate substantially equal to a flow rate of the gas mixture delivered to the skin surface.

6. The method of claim 4, further comprising stripping one or more of nitric oxide and nitric dioxide from the evacuated gas mixture.

7. The method of claim 1 further comprising diluting the gas mixture.

8. The method of claim 1, further comprising adjusting the pressure of the gas mixture delivered to the treatment site.

9. The method of claim 1, further comprising controlling the flow rate of gas mixture into and out of the bathing unit.

10. The method of claim 1, wherein the treatment site is a wound.

11. The method of claim 10, wherein the wound is selected from the group consisting of a surgical wound, a trauma wound, a burn and a combination thereof.

12. The method of claim 1, wherein the treatment site is a lesion.

13. The method of claim 12, wherein the lesion is selected from the group consisting of a surgical wound, a trauma wound, a burn, an abscess, an actinic keratosis, a keloid, a scar, skin cancer and a combination thereof.

14. The method of claim 1, wherein the treatment site is an infection site.

15. The method of claim 14, wherein the infection site is infected by at least one pathogen selected from the group consisting of a bacterium, a virus, a fungus, a parasite, an arthropod, a protozoan, and an antibiotic resistant bacterium.

16. The method of claim 1, wherein the subject has an inflammatory disorder, and wherein the treatment site is affected by the inflammatory disorder.

17. The method of claim 16, wherein the inflammatory disorder is selected from the group consisting of psoriasis, dermatitis, eczema, rosacea and a combination thereof.

18. The method of claim 1, wherein the subject is in need of enhanced blood flow at the treatment site.

19. The method of claim 1, wherein the subject is in need of enhanced collagen synthesis at the treatment site.

20. The method of claim 1, wherein the subject is in need of angiogenesis at the treatment site.

21. The method of claim 1, wherein the subject is in need of hair growth at the treatment site.

22. The method of claim 1, wherein the subject has erectile dysfunction.

23. The method of claim 1, wherein the subject has erectile dysfunction and is in need of enhanced blood flow at the treatment site.

24. The method of claim 1, wherein nitric oxide concentration in the gas mixture containing nitric oxide are 1 ppm to 40,000 ppm.

25. The method of claim 1, wherein the pressure of the gas mixture containing nitric oxide ranges from 1.0 atmosphere to 3.5 atmospheres.

26. The method of claim 1, wherein the gas mixture containing nitric oxide is delivered to the treatment site at a flow rate of 0.25 liters per minute to 1.0 liters per minute.

27. The method of claim 1, wherein the gas mixture containing nitric oxide is delivered to the treatment site between 10 minutes to 8 hours.

28. The method of claim 1, wherein nitric oxide concentration in the gas mixture containing nitric oxide is 10,000 ppm, the pressure of the gas mixture containing nitric oxide is 1.5 atmosphere and wherein the gas mixture containing nitric oxide is delivered to the treatment site continuously for at least 30 minutes.

29. The method of claim 1, further comprising evacuating the gas mixture from the treatment site through at least one outlet on the bathing unit while the gas mixture is being transported to the bathing unit.

\* \* \* \* \*